United States Patent
Raimondi et al.

(10) Patent No.: US 11,027,045 B2
(45) Date of Patent: Jun. 8, 2021

(54) SYNTHETIC NICHE MATRICES FOR STEM CELL CULTURE

(71) Applicants: POLITECNICO DI MILANO, Milan (IT); CONSIGLIO NAZIONALE DELLE RICERCHE, Milan (IT); FONDAZIONE CARIPLO, Milan (IT)

(72) Inventors: Manuela Teresa Raimondi, Milan (IT); Giulio Cerullo, Milan (IT); Roberto Osellame, Milan (IT); Andrea Remuzzi, Bergamo (IT)

(73) Assignees: POLITECNICO DI MILANO, Milan (IT); CONSIGLIO NAZIONALE DELLE RICERCHE, Milan (IT); FONDAZIONE CARIPLO, Milan (IT)

( * ) Notice: Subject to any disclaimer, the term of this patent is extended or adjusted under 35 U.S.C. 154(b) by 558 days.

(21) Appl. No.: 15/755,011

(22) PCT Filed: Aug. 31, 2016

(86) PCT No.: PCT/EP2016/070500
§ 371 (c)(1),
(2) Date: Feb. 23, 2018

(87) PCT Pub. No.: WO2017/037108
PCT Pub. Date: Mar. 9, 2017

(65) Prior Publication Data
US 2020/0046881 A1  Feb. 13, 2020

(30) Foreign Application Priority Data

Sep. 4, 2015 (IT) .................. 102015000048704

(51) Int. Cl.
| | | |
|---|---|---|
| A61L 27/38 | (2006.01) | |
| A61L 27/56 | (2006.01) | |
| C12N 5/00 | (2006.01) | |
| C12N 5/0735 | (2010.01) | |
| C12N 5/0775 | (2010.01) | |

(52) U.S. Cl.
CPC ......... *A61L 27/3834* (2013.01); *A61L 27/56* (2013.01); *C12N 5/0068* (2013.01); *C12N 5/0606* (2013.01); *C12N 5/0663* (2013.01); *A61L 2400/18* (2013.01); *C12N 2533/30* (2013.01); *C12N 2535/00* (2013.01)

(58) Field of Classification Search
CPC .................................................. A61L 27/3834
See application file for complete search history.

(56) References Cited

PUBLICATIONS

Raimondi et al. (Acta Biomaterialia 9 (2013) 4579-4584) (Year: 2013).*
Guven et al. (Trends in Biotechnology, May 2015; 33(5):269-279). (Year: 2015).*
Raimondi et al., "Optimization of femtosecond laser polymerized structural niches to control mesenchymal stromal cell fate in culture" Micromachines, 2014, v 5, p. 341-358.
Maciulaitis et al., "Preclinical study of SZ2080 material 3D microstructure scaffolds for cartilage tissue engineering made by femtosecond direct laser writing lithography" Biofabrication, 2015, v 7.
Nava et al., "Interactions between structural and chemical biomimetism in synthetic stem cell niches" Biomedical Materials, 2015, v 10.
Pellegrini, International Search Report for PCT/EP2016/070500 dated Dec. 6, 2016.

* cited by examiner

*Primary Examiner* — Scott Long
(74) *Attorney, Agent, or Firm* — Greer, Burns & Crain, Ltd; Gregory P. Einhorn

(57) ABSTRACT

The present invention relates to a supermatrix of synthetic niches comprising at least two matrices of niches wherein each matrix comprises n×m niches and wherein the distance (d) between a matrix and the other is greater than zero and wherein in each matrix every synthetic niche has one or more walls in common with the others synthetic niches of the matrix.
A support for the culture of cells that includes at least one supermatrix and the use of said supermatrix or support for the in vitro culture of cells, in particular stem cells, or for the in vivo implant in a subject in order to promote tissue or organ regeneration through cell repopulation are also within the scope of the present invention.

20 Claims, 11 Drawing Sheets

Figure 1:
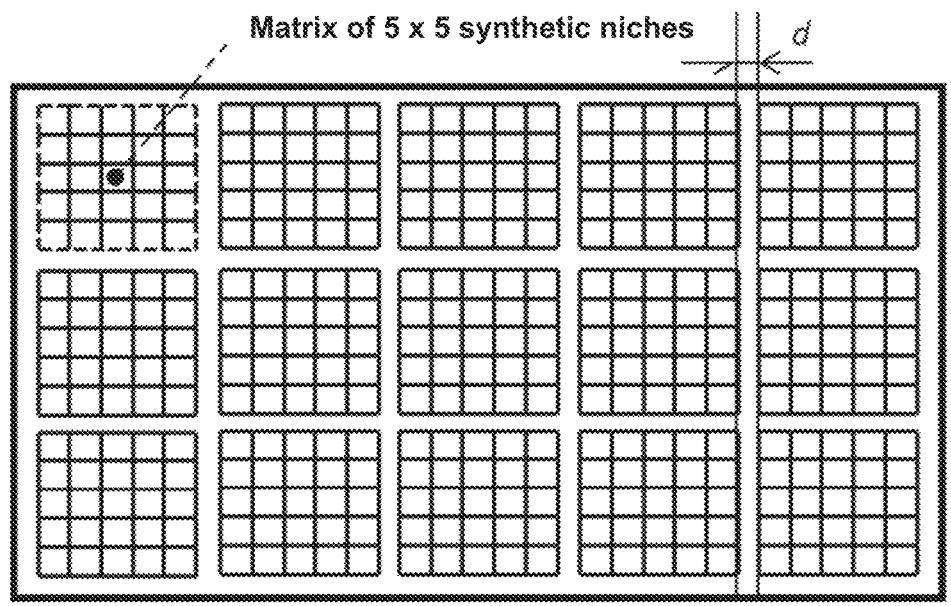

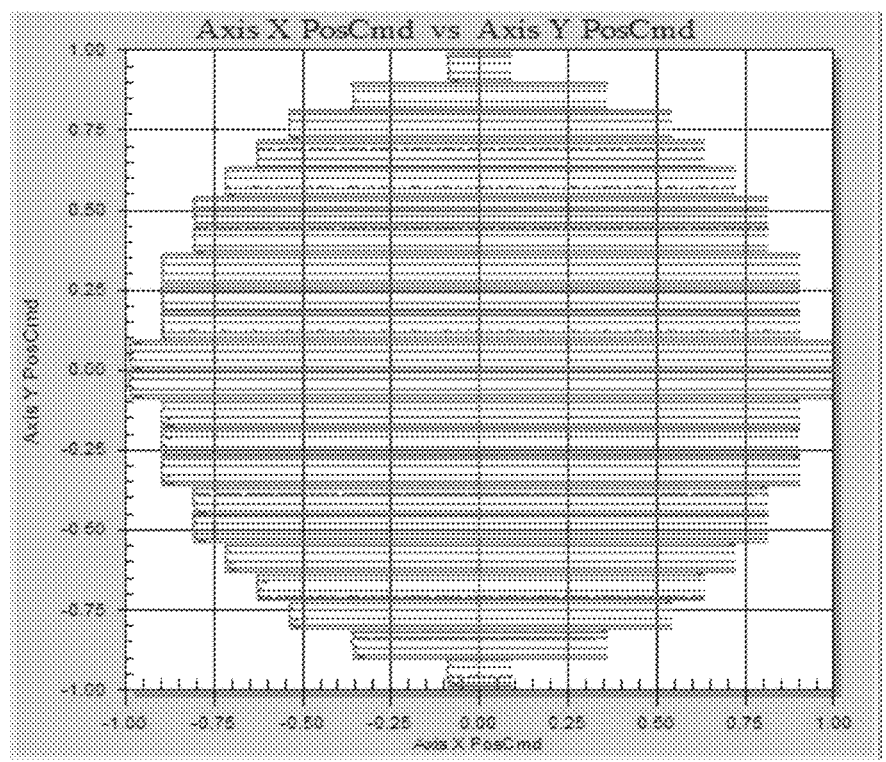
FIGURE 11.1
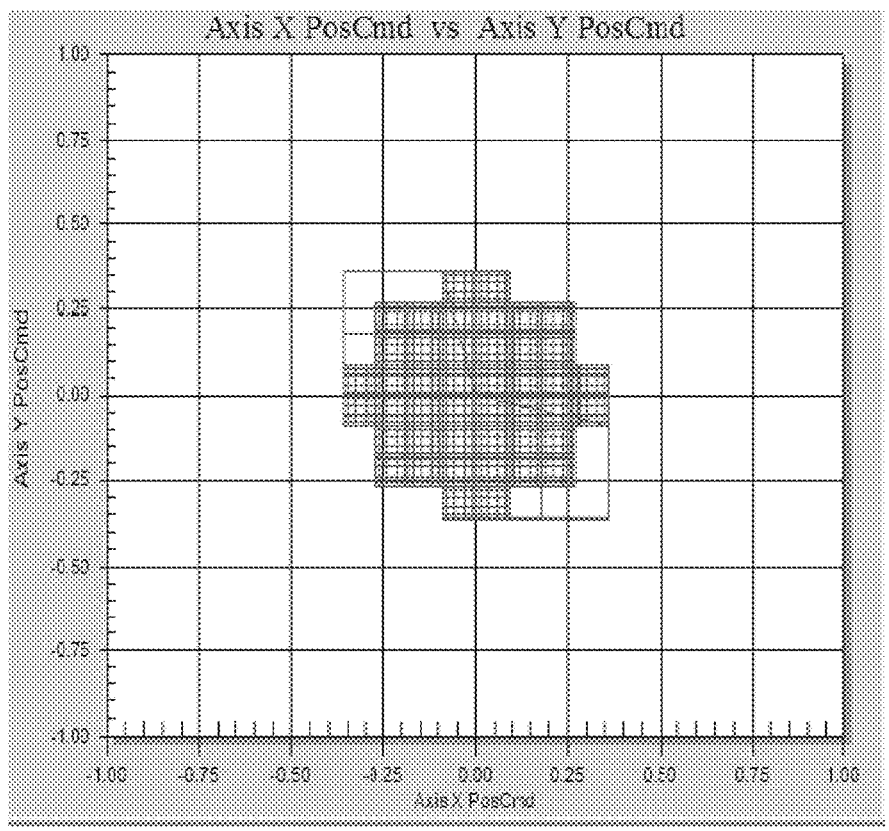
FIGURE 11.2

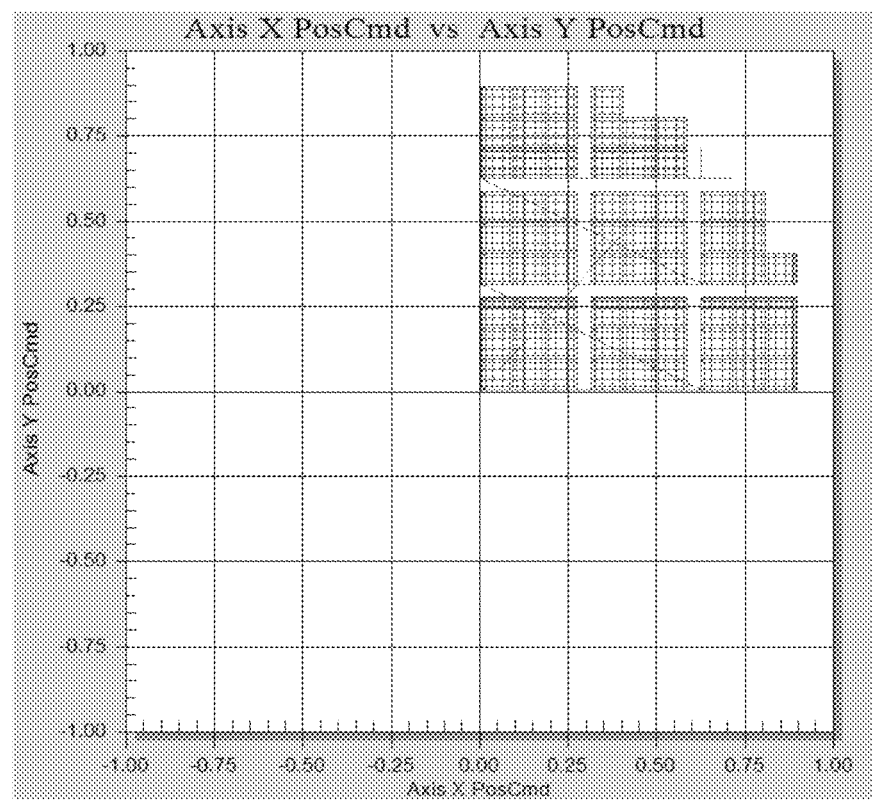
FIGURE 11.3
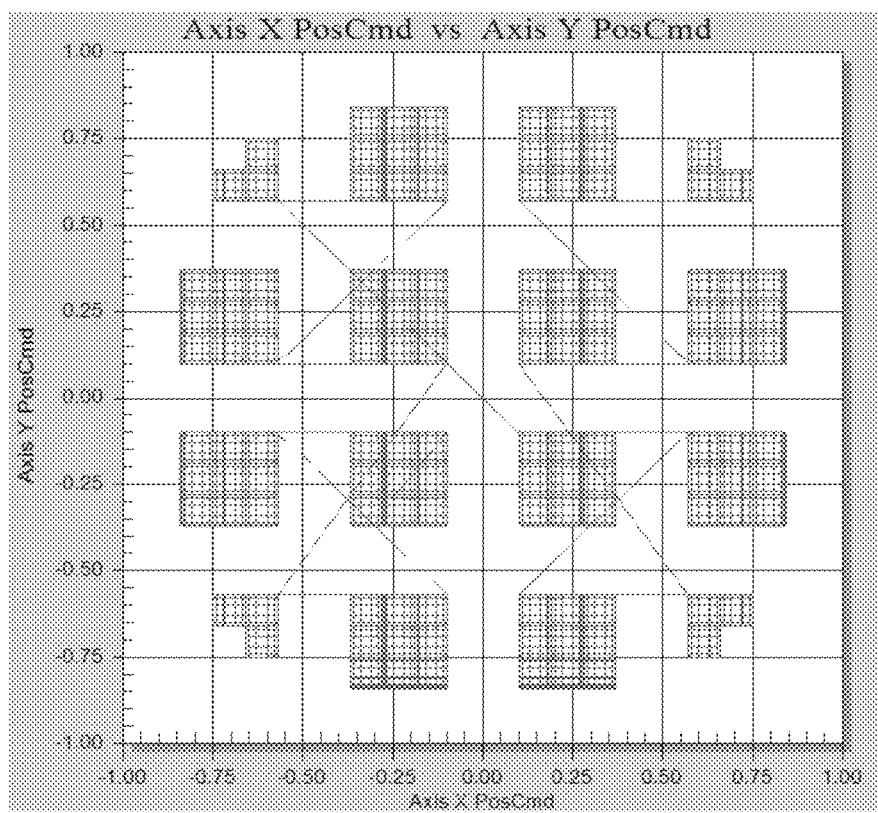
FIGURE 11.4

SYNTHETIC NICHE MATRICES FOR STEM CELL CULTURE

This application is a national phase application claiming benefit of priority under 35 U.S.C. § 371 to International (PCT) Patent Application serial number PCT/EP2016/070500 filed Aug. 31, 2016, which claims benefit of priority to Italian patent application serial number 102015000048704, filed Sep. 4, 2015. The aforementioned applications are expressly incorporated herein by reference in their entirety and for all purposes.

FIELD OF THE INVENTION

The project that led to this patent application was funded by the European Research Council (ERC) in the context of the European Union Research and Innovation Program Horizon 2020 (grant agreement No. 646990-NICHOID)".

The present invention relates to a support for cell culture, in particular of stem cells.

More in particular, the present invention relates to a three-dimensional structure comprising matrices of synthetic niches.

Said invention has application in particular in the field of regenerative medicine and tissue engineering.

BACKGROUND OF THE INVENTION

Regenerative medicine adopts living cells in treatments developed to repair injured or diseased cell tissues. Whenever such cells are associated with matrices that support their regeneration, the regenerative strategy is referred to as tissue engineering.

The aim is to replace injured organs or tissues by culturing cells taken from patients on a support in cultures suitable for the formation of an engineered tissue to be implanted in the patient.

The basic strategy usually adopted is to isolate a cell population from a patient and to expand it in vitro, seeding the cells on a suitable support known as a "scaffold". This porous structure guides the development of the tissue and provides temporary structural support up until when it is implanted in the patient, after which the support is left to degrade or remain in place.

Isolated cells, indeed, do not have the capacity to maintain tissue architecture because they lack a support that drives them. In addition to merely providing support, the scaffold must be capable of promoting the growth and differentiation of the cells that adhere to it, and must have determined mechanical characteristics that vary depending on the type of cell being cultured.

On the basis of the interactions between the extra cellular matrix and the cells that the scaffold must simulate, it must have the following biological properties:

Cyto-compatibility: this is the most important characteristic that a scaffold must possess in order for in vitro studies to be performed. Together with this property, also biocompatibility is required; after it has been implanted, the scaffold must not be toxic and must be capable of absorbing the molecules of the Extra Cellular Matrix (ECM) in such way that they eventually replace it. In vivo studies also require a good degree of biodegradability in order to permit scaffold residues to be expelled from the organism without causing undesired accumulations in the implantation area.

Three-dimensionality: the scaffold must prove capable of re-creating the three-dimensional (3D) environment of the ECM. The pores must be sized in such way as to permit both cellular activities and the passage of nutrients. Scaffolds with high porosity and spacious pore sizes are therefore desirable, without this compromising the stability of the structures and the adhesion of the cells.

stiffness: elasticity modulus and the degradation methods bear fundamental importance because they influence both the mechanical strength of the scaffold and the differentiation and proliferation of the cells.

Another necessary characteristic is that the scaffold must not affect sample analysis. Scaffold signals sometimes mask or disturb signals from cells, especially during optical microscopy measurements (fluorescence and other types), in this way seriously compromising the study of culture results.

Thanks to their capacity to differentiate into different phenotypes and to be expanded in vitro, stem cells are a potential solution to various problems in regenerative medicine, such as the scarcity of organs for transplants.

The current impossibility to maintain stem cells undifferentiated, particularly adult stem cells, in prolonged culture poses an important limit on their potential application in the field of regenerative medicine and tissue engineering.

Promoting and supporting self-renewal in vitro is essential in developing and maintaining culture lines with stem cells. Indeed, whenever conditioning suited to maintain them as such is lacking, these cells inexorably tend to differentiate.

The maintenance of stemness in vitro has been conventionally promoted by chemical means through the addition of suitable substances to the culture medium.

Greater knowledge of these cells in recent times has led to the emergence of an innovative concept based on physical conditioning alone.

In particular, links between stem cell behavior and surface patterns of the support culture are now being studied.

In the human body, adult stem cells are located inside tissues in sites known as stem cell niches that constitute the microenvironment in which the cells live, proliferate, and differentiate.

In the same way, an artificial scaffold should be capable of controlling cell proliferation and, more importantly, differentiation: the cells can remain in quiescent state until an external stimulus induces them to divide and differentiate into specialized cells.

Stem cell niche engineering also offers an excellent means of shedding light on the mechanisms that regulate cell behavior in vivo, given that it provides cells with a space in which they are confined and artificially stimulated to maintain stemness, exactly as happens in the human organism. This would permit the guiding of stem cell behavior through mechanical interaction only, in this way providing a solid basis for the use of stemness induction in clinical practice.

A scaffold that allows stem cells to proliferate while at the same time remaining in their undifferentiated state is therefore desired.

3D scaffolds in natural polymers and synthetic polymers are known.

The natural polymers adopted so far that have been shown capable of making effective contributions to the maintenance of stemness include hyaluronic acid, collagen, and chitosan.

The scaffolds in synthetic polymer material used to promote stemness are generally composed of biodegradable polymers, such as polylactic acid (PLA), polyglycolic acid (PGA) and their copolymer form, PLGA.

The traditional scaffolds do not offer cells a truly 3-D culture environment, given that most scaffolds have pores with dimensions orders of magnitude greater than those of cells, with the result that the cells do not perceive the three-dimensionality of these structures whose surfaces are essentially two-dimensional on a micrometric scale.

It is therefore necessary to artificially modulate on a micro-scale the interaction between the cells and the support on which they are seeded by fabricating three-dimensional structures with controlled dimensions at the scale of single cells.

The only known fabrication technology that permits this type of structure to be obtained is two-photon laser polymerization (2PP), which permits the creation of 3D scaffolds with sub-micrometric precision.

So-called non-traditional micro-fabrication techniques allow to obtain scaffolds with controlled, and above all, pre-defined micro-structure, often allowing the structure to be developed by starting from a Computer-Aided Design (CAD) model.

The most widely adopted techniques are lithographic, such as photolithography, soft-lithography, stereo-lithography, x-ray lithography, and electronic lithography (e-beam lithography).

Photolithography is one of the most important technologies in the fabrication of structures on micro-scale, and is a process used to selectively remove parts of a slender film or substrate. It uses a beam of light to transfer a geometrical pattern from a photomask to a photosensitive chemical substance (photosensitive resin or photoresist) deposited over the substrate. The photomask is a sheet, usually in quartz, that is coated by a metallic layer in order to generate areas of transparency or opacity in the geometric pattern to be reproduced. Subsequent chemical or physical treatments model the pattern on the material. Exposure transfers the pattern of the desired characteristics by means of the photomask positioned between the substrate, covered by a photosensitive material (photoresist), and the light source. Subsequently, the material can be removed from the substrate using chemical techniques (etching). Photolithography is an intrinsically two-dimensional (2D) technique.

Selective Laser Sintering (SLS) technique instead permits the fabrication of three-dimensional structures through the action of a laser beam on layers of material in the form of powder. The scaffold is designed and a three-dimensional CAD model is produced; the fabrication process is very similar to that of 3D printing: a fine layer of powder is used and irradiated by an infrared laser (typically a $CO_2$ laser) in order to sinter the particles in the desired form and create an initial layer of the structure. The structure is then lowered and the process is repeated until the scaffold is completed; the non-sintered powder is eliminated. Several studies have demonstrated the possibility to fabricate scaffolds in polycaprolactone (PCL) and calcium-phosphate compounds that possess the adequate mechanical and morphological characteristics for cell growth.

However, this technique offers a spatial resolution of the order of hundreds of microns and for such reason is not suited to fabricate 3D scaffolds of dimensions compatible with those of cells.

The only known fabrication technique that provides sub-micrometric control over scaffold geometry in 3D is 2PP, which can be used to obtain structures with controlled geometry to sub-micrometric precision by irradiating a photosensitive material with a highly focalized pulsed infra-red laser beam. The simultaneous absorption of two laser photons triggers a photochemical process that causes the polymerization of the focal volume, in this way permitting the definition inside the material of an element of volume (volume pixel, voxel) with transversal and longitudinal resolution lower than the wavelength.

Thanks to its enormous potential, the 2PP technique meets the need to create three-dimensional scaffolds whose geometry and micro/nano surface patterns are highly controllable. In recent years, a growing number of researchers has adopted this technique in the fabrication of scaffolds for cellular growth. Most studies in scientific literature aim to demonstrate the biocompatibility of the material used and to assess cell behavior in respect to the characteristics of the scaffolds developed; clinical applications of structures fabricated using 2PP, instead, are not yet available. Numerous studies conducted on scaffolds fabricated using 2PP (Karl-Heinz Haas and Herbert Wolter. Synthesis, properties and applications of inorganic-organic copolymers. Current Opinion in Solid State and Materials Science, 4(6):571-580, 1999; Thomas Weill, Ronald Schade, Thorsten Laube, Albrecht Berg, Gerhard Hildebrand, Ralf Wyrwa, Matthias Schnabelrauch, and Klaus Liefeith. Two-photon polymerization of biocompatible photopolymers for micro-structured 3d biointerfaces, Advanced Engineering Materials, 13(9):B264-B273, 2011) confirm the potential of this technology, which permits the creation of structures for stem cell growth and the study of cell behavior in light of future clinical applications in regenerative medicine.

2PP technique is therefore promising for applications of biological nature in which 3D structures with spatial resolutions of only a few micrometers must be prepared, and in particular, for tissue engineering, in which the development of techniques that enable the control of many different aspects of cell behavior, such as adhesion, migration, proliferation and differentiation is highly important.

Structures obtained through 2PP have enormous potential in regenerative medicine: a simple, ordered micro-structure composed of parallel microfibers is already capable of physically directing the regeneration of neural tissue (Vasileia Melissinaki, A A Gill, Ilida Ortega, Maria Vamvakaki, Anthi Ranella, J W Haycock, C Fotakis, M Farsari, and F Claeyssens. Direct laser writing of 3d scaffolds for neural tissue engineering applications. Biofabrication, 3(4): 045005, 2011) or guiding the orientation of human fibroblasts (L E Sima, E C Buruiana, T Buruiana, A Matei, G Epurescu, M Zamfirescu, A Moldovan, S M Petrescu, and M Dinescu. Dermal cells distribution on laser-structured ormosils. Journal of tissue engineering and regenerative medicine, 7(2):129-138, 2013).

2PP has permitted the fabrication of ultra-precise and ordered structures with geometry controlled at cellular scale (10 μm) and extremely high spatial resolution (less than 1 μm).

This technique has already been employed to fabricate scaffolds expressly designed for cell interaction. Over the last twenty years, in fact, biophysical factors have been shown capable of influencing the biological response of cells in culture, even in the absence of biochemical factors (Manuela Teresa Raimondi. Engineered tissue as a model to study cell and tissue function from a biophysical perspective. Current drug discovery technologies, 3(4):245-268, 2006).

Biopolymer scaffolds fabricated through 2PP adequately mimic the cellular micro-environment in architectural terms, but often lack the necessary mechanical stability.

Some patent literature relates to the fabrication of 3D scaffolds, also for cell culture.

WO2012018304, for example, discloses a method for the fabrication of a three-dimensional scaffold comprising encapsulated cells. The method uses two-photon laser photolithography. In this method, the cells are encapsulated during the formation of the 3D structure in order to avoid the need for the cell seeding procedure. The scaffold was not tested on stem cells but on endothelial and hepatic cells, therefore the problem of maintaining stem cell pluripotency was not addressed.

WO2009048314 discloses 3D structures fabricated through laser photo-polymerization in which cells proliferate. However, these are structures that can be implanted in vivo for the regeneration of bone and cartilage and not substrates for in vitro cell culture. Therefore, they are designed for the creation of osteo-inductive and osteo-conductive environments.

US20070249044 discloses a 3D system for cell culture comprising micro-structures suspended in a cell culture gel. These are polymeric structures used for fibroblast culture. Here as well, however, the issue of stem cell growth is not addressed.

WO2012041522 describes a method for the production of layered 3D structures that can be used in cell culture. The problem of creating synthetic niches for stem cell growth is not addressed.

The utilization of 2PP technique in preparing 3D substrates that are useful in tissue engineering is known.

For example, Malinauskas, M., Danilevičius, P., Baltriukiene, D., Rutkauskas, M., ukauskas, A., Kairyte, Z., Bičkauskaite, G., Purlys, V., Paipulas, D., Bukelskiene, V., and Gadonas, R. in "3D artificial polymeric scaffolds for stem cell growth fabricated by femtosecond laser", 2010, Lithuanian Journal of Physics, Vol. 50, No. 1, pp. 75-82, describe 3D scaffolds for the proliferation of cells, also stem cells. Ovsianikov, A., Malinauskas, M., Schlie, S., Chichkov, B., Gittard, S., Narayan, R., Löbler, M., Sternberg, K., Schmitz, K.-P., and Haverich, A., in "Three-dimensional laser micro- and nano-structuring of acrylated poly (ethylene glycol) materials and evaluation of their cytoxicity for tissue engineering applications", 2011, Acta Biomaterialia, 7 (2011) 967-974, studied 3D structures for applications in tissue engineering. Mačiulaitis J, Deveikytė M, Rekštytė S, Bratchikov M, Darinskas A, Šimbelytė A, Daunoras G, Laurinavičienė A, Laurinavičius A, Gudas R, Malinauskas M, Mačiulaitis R. in "Preclinical study of SZ2080 material 3D microstructured scaffolds for cartilage tissue engineering made by femtosecond direct laser writing lithography." Biofabrication. 2015 Mar. 23; 7(1), study 3D artificial microscaffolds for culture of chondrocytes to form cartilage-like tissue.

All such 3D structures were designed for use as scaffolds into which cells can be inserted and proliferate with the purpose of creating artificial tissues that are as similar as possible to natural tissues. In these 3D structures, the single units composing the scaffold all communicate completely one with another: therefore the cells are free to migrate from one unit to another of the scaffold. This highly influences their behavior. Although the biocompatibility of such scaffolds and their suitability for use in tissue engineering was shown, the problem of maintaining stem cells in indifferentiated state was not addressed. On the contrary, these studies address the problem of differentiating the cells into cells of the desired tissue.

Therefore, scaffolds suited to promote the proliferation of stem cells while at the same time impeding or decelerating their differentiation are still highly desired. Moreover, scaffolds of prior art have a small extension and therefore do not address the problems of mechanical stability that emerge when millimeter-sized surfaces must be covered. Secondly, the absence of physical confinement inside single units in traditional scaffolds has never allowed to demonstrate the maintenance of cell stemness but instead their differentiation inside such structures.

The effect of various scaffold geometries on mesenchymal stem cell behavior has recently been studied.

Works by Raimondi et al. (Three-dimensional structural niches engineered via two-photon laser polymerization promote stem cell homing. Manuela T. Raimondi, Shane M. Eaton, Matteo Laganà, Veronica Aprile, Michele M. Nava, Giulio Cerullo, Roberto Osellame: Acta Biomaterialia, 2013, Vol. 9, pp. 4579-4584; Optimization of direct laser-written structural niches to control mesenchymal stromal cell fate in culture. M. T. Raimondi, M. M. Nava, S. M. Eaton 2, A. Bernasconi, K. C. Vishnubhatla, Giulio Cerullo, R. Osellame: Micromachines, 2014, Vol. 5, pp. 341-358) describe structures, referred to as synthetic niches, composed of a polymeric resin known as SZ2080 that was expressly developed for 2PP (Materials Processing: Two-photon fabrication. M. Farsari, B. N. Chichkov: Nature Photonics, 2009, Vol. 3). These structures are referred to as synthetic niches because they artificially reproduce the stem cell niches environment. The definitive morphology of the scaffold was selected by optimizing parameters such as "homing", i.e. the capacity of the niche to promote the entry of the cells and their maintenance inside it, along with cellular proliferation and adhesion. The earliest studies on this 3D scaffold were conducted using multipotent primary mesenchymal stem cells (MSC) isolated from bone marrow taken from rat femurs. The results obtained confirm that the matrix is capable of maintaining a more roundish cell nuclei morphology than that of 2D flat cultures. The most significant result is that after prolonged culture (3 weeks) the cells show differences in behavior between 2D and 3D environments: marked cellular differentiation towards bone phenotype takes place outside the niche, in fact, whereas inside the niche, the cells are negative for the differentiation staining performed and present higher Ki67 expression than in monolayer culture, and this is indicative of superior proliferative capacity maintenance. The optimized niche geometry was able to supply the stem cells with a higher surface area/volume ratio that allowed them to adhere and proliferate while maintaining multipotency (Raimondi et al. 2013, 2014).

In view of potential applications in clinical practice, the use of purely mechanical cues in guiding stem cell behavior has the important advantage of minimizing the use of biochemical molecules, e.g. growth factors, in this way reducing risks to the patient posed by their administration.

However, one problem that still remains to be solved is how to significantly increase the surface area covered by the synthetic niches.

Previous studies on similar structures led to the hypothesis that biodynamics are influenced not only by geometry but also by the distance between individual synthetic niches.

In studies by Raimondi et al. (2013 and 2014), for example, niche patterns were fabricated with different distributions in space with a hexagonal configuration. More in particular, sample structures were fabricated in which 6 niches were arranged at the vertexes of a hexagon with 200-600 µm sides and another structure was positioned at the center in such way that all were equidistant. In tests with MSC, the micro-structured niches were observed to be capable not only of promoting stem cell homing but also of guiding the formation of cell aggregates.

Nava et al. (Interactions between structural and chemical biomimetism in synthetic stem cell niches. Michele M Nava, Manuela T Raimondi, Caterina Credi, Carmela De Marco, Stefano Turri, Giulio Cerullo and Roberto Osellame. Biomed. Mater. 10 (2015) 015012) describe synthetic niches arranged in a triangular pattern at 200 µm distance coated with hydrogel and tested with rat mesenchymal stem cells.

Figure 7:
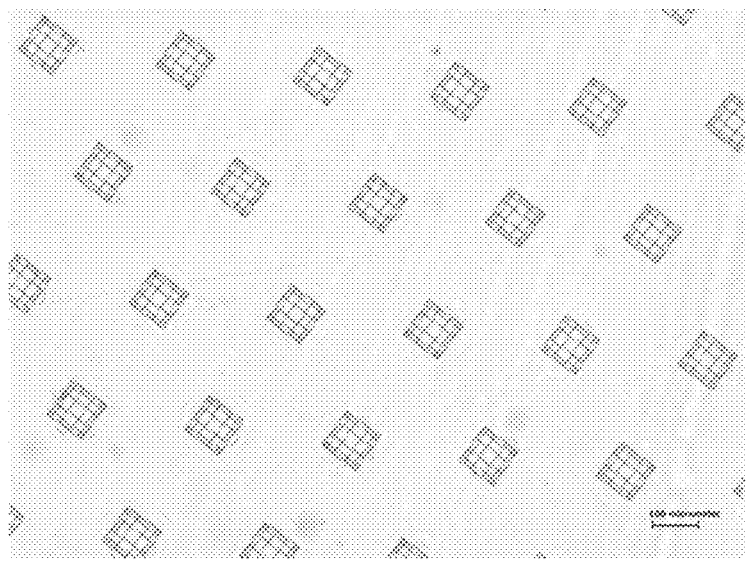

The structures described in the state of the art above mentioned have the disadvantage of leaving a large amount of support surface space free from synthetic niches (see FIG. 7). On such free surface area, the cells behave in a two-dimensional manner, therefore they differentiate rapidly, losing their sternness.

In order to permit the commercial use of 3D structures as culture substrates on a wide scale, and therefore for the culture of millions of cells, the support surface covered by the synthetic niches must be as large as possible.

The synthetic niches proposed in the state of the art do not solve the problem because the niches cover a limited surface area of 10% of the total support surface area available for cellular adhesion. Therefore they can be used for 3D culture of very low numbers of cells, and this places a serious limit on industrial and commercial applications.

Increasing the surface area covered by micro-structures requires a structure that minimizes the contribution of flat surfaces between the individual niches.

Therefore there is the need to fabricate a single large structure, still with a micro-structure, capable of hosting in itself the highest possible number of cells in order to eliminate two-dimensional behavior completely or at least to the greatest possible extent.

In order to obtain higher scaffold surface density, a set of synthetic niches in which a continuous lattice produced by the pairing of single niches entirely covering a 6 mm diameter circular region was produced. This permits to maximize the area covered by the scaffold and to cover 96% of the total surface.

However, the fabrication of this type of structure produces various defects due to the shrinkage of the polymer material that deforms the structure, and also to cavitation, which leads to the formation of bubbles and the consequent rupture of the structure (see FIG. 4B-C).

In particular, the construction of one, single larger structure that hosts multiple synthetic niches poses the problem of the shrinkage of the polymer during expansion (FIG. 4B) that creates mechanical stress and deformation. The excessive dimensions of the surface covered by the structures pose the risk of damaging some areas in the niches with repercussions on the rest of the structure.

Furthermore, these structural damages compromise the interaction between the structures and the cells.

For this reason, there is still the need of developing uniform, defined and unbroken, intact matrices that maintain the three-dimensional structure required for cell proliferation and at the same time maximize the surface over which the cells can proliferate while remaining undifferentiated.

It has now been found that by grouping synthetic niches in separate matrices, any slight shrinkage that occurs in the polymer composing the synthetic niches does not ruin the entire structure, particularly because it is not superimposed to the shrinkage of adjacent matrices thanks to the distance between each other.

Figure 4:
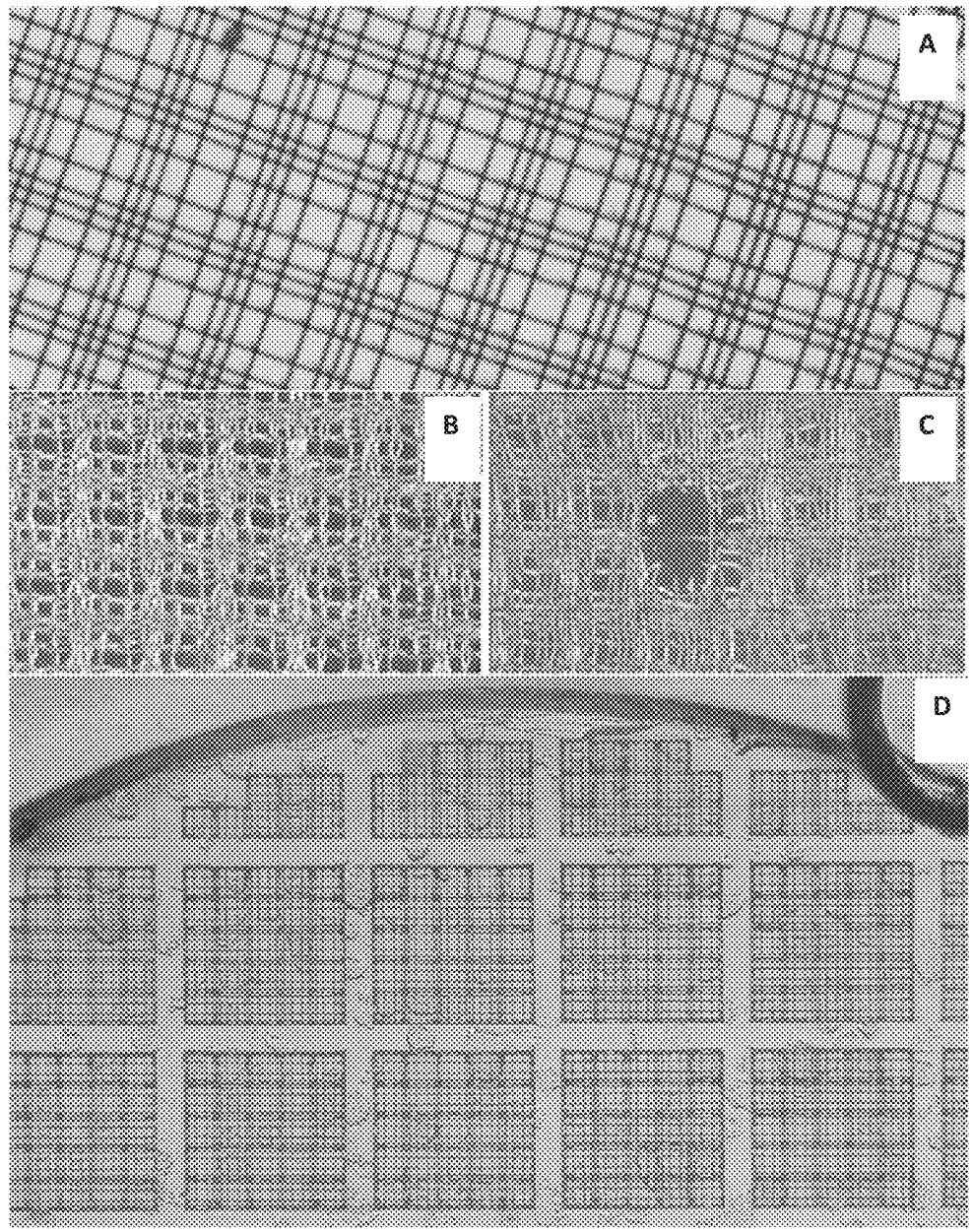
Figure 5:
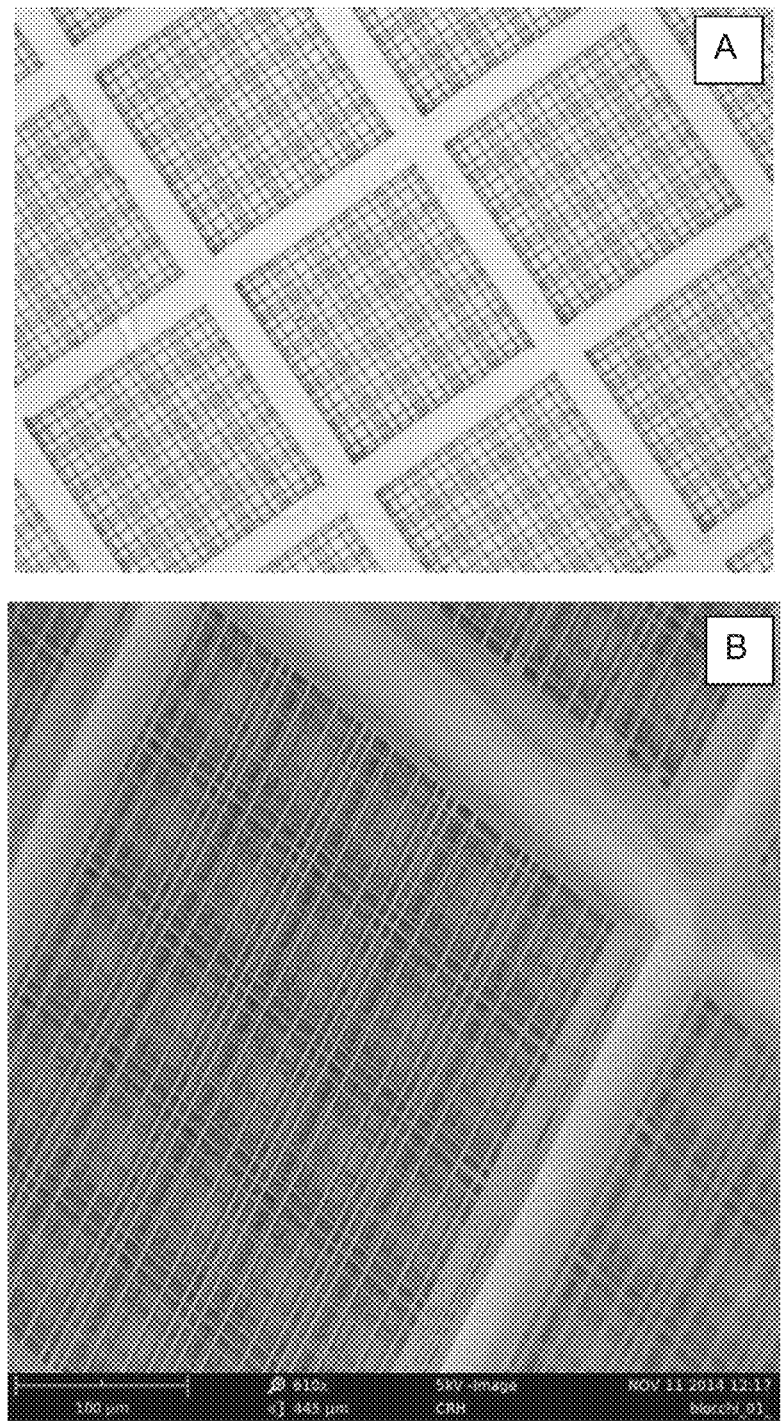

It has therefore been found a 3D cell culture structure, herein referred to as supermatrix, composed of matrices of synthetic niches with a determined configuration that presents the advantages of a stronger and more stable structure than the one described in prior art, in particular, a structure in which no deformations or defects are present and in which at the same time the three-dimensional structure of the engineered niches is maintained (see, for example, FIG. 4D and FIG. 5 A-B).

Indeed, in the structure according to the present invention, the damages caused by the shrinkage of the polymer described above do not occur.

Furthermore, the use of a supermatrix of synthetic niches composed in this way ensures, for example, that any disruption and/or detachment of a niche matrix does not damage the niche matrices nearby in such way that even when two-dimensional behavior of the cells seeded is observed in such area, it may be considered negligible because it does not influence the development of the culture in the other matrices.

The 3D structure object of the present invention also permits to obtain reproducible engineered niches.

Furthermore, thanks to their stability, these supermatrices can be re-utilized.

Using the supermatrix according to the invention as a substrate for multipotent or pluripotent cell culture permits potency maintenance without continuously inserting chemical factors that condition the cells in the culture medium. The difference between using chemical factors and using synthetic niches lies, in fact, in the different duration of the differentiating change: cells usually remain pluripotent only if chemical factors are inserted frequently, whereas with the use of the supermatrix according to the invention, both multipotency and pluripotency are able to be maintained even after many divisions of the first stem cell seeded.

The supermatrices according to the invention are therefore suited to the culture of any type of stem cell, in particular adult stem cells, more in particular mesenchymal, and embryonic stem cells.

More in particular, the effectiveness of such supermatrices of synthetic niches has been assessed in adult mesenchymal stem cells (multipotent) and in embryonic stem cells (pluripotent).

SUMMARY OF THE INVENTION

It is an object of the present invention a supermatrix comprising at least two matrices of synthetic niches,
- wherein each matrix comprises n×m synthetic niches, wherein n and m, the same or different from each other, have a value ≥1, provided that one of m or n is ≥2 and with a maximum value of m and n which allows to maintain the structure of the single synthetic niche intact such that shrinking of the material does not cause significant disruptions, and
- wherein the distance (d) between a synthetic niche matrix and the other is greater than zero, and
- wherein in each matrix every synthetic niche has one or more walls in common with the other synthetic niche(s) of the matrix.

Preferably, said maximum value for n and m is 100.

Preferably, m and n are the same and each matrix has a square form.

In an exemplary embodiment according to the invention, m and n are both equal to 5, so that every synthetic niche matrix is a 5×5 matrix (5 synthetic niches×5 synthetic niches).

In a preferred embodiment, the height of the supermatrix is comprised between 30 and 100 µm. This permits the use of all known techniques for the analysis of the cells, regardless of their differences in terms of dimension, deformability, and substrate adherence kinetics among the various stem cell populations.

The supermatrix according to the invention is obtained using the two-photon laser polymerization (2PP) technique.

It is also an object of the invention a substrate or support for cell culture that comprises at least one supermatrix according to the invention.

Said support is, for example, a mono- or multi-well culture plate or a flask.

The use of the supermatrix according to the invention for stem cell culture, particularly in vitro, is another object of the present invention.

Said cells are preferably adult stem cells. In another embodiment, they are embryonic stem cells.

In another embodiment, the supermatrix according to the invention is used for in vivo implant in a subject in order to promote tissue regeneration.

It is a further object of the invention the use of the supermatrix of the invention or of the culture support comprising it for cell culture analysis, in particular, in the diagnostics field.

The supermatrix according to the invention has the main advantage of allowing the increase of the surface available for cell culture covered by niches.

This permits an extension of its use in both wide-scale biological research and in the clinical applications of cells cultured as therapeutic products.

The use of said supermatrix allows obtaining an intact three-dimensional structure in which no damage is caused by the shrinking of the polymer during expansion.

Thanks to the maintenance of a perfectly 3D environment, the synthetic niches according to the invention can induce nuclei conformations such to prevent or significantly delay stem cell differentiation, unlike encapsulation or seeding on natural 3D polymer substrates, which do not guarantee the same degree of geometrical control.

Compared to known 3D structures, such as those of Maulinaskas et al., 2010 and 2011, for example, in the supermatrix according to the invention, every synthetic niche is surrounded by an external perimeter that is permeable to the diffusion of molecules but obstacles the migration of cells from one synthetic niche to the adjacent ones. This permits to address and solve the problem of maintaining pluripotency and delaying differentiation of stem cells.

Furthermore, contrary to the observation in prior art, said delay of differentiation has been observed to take place without chemical conditioning, in this way demonstrating that in the supermatrix according to the invention, mechanical cues are necessary and sufficient to promote pluripotency and inhibit differentiation.

Moreover, said supermatrix permits reductions in production times, an essential requirement for the scale-up of the process and in particular for mass production.

As an additional advantage, the same supermatrix can be used again in subsequent experiments without requiring the production of new structure samples for every new use.

In addition, thanks to complete reproducibility structures identical one to another are obtained: 3D matrices in collagen, chitosan, hyaluronic acid or synthetic polymers instead present marked structural variations even under equivalent conditions of production.

The supermatrix according to the invention is particularly useful in the field of regenerative medicine and tissue engineering, where it can be used to provide a number of cells sufficient for applications involving the repopulation of decellularized organs or in situ treatments, for example.

DETAILED DESCRIPTION OF THE INVENTION

Definitions

In the context of the present invention, the term supermatrix means a three-dimensional structure comprising more than one synthetic niche or synthetic niche matrices.

In the context of the present invention, the term synthetic niche means a synthetic three-dimensional structure suited to reproducing the geometric constraints to which stem cells are subjected in their native micro-environment (the stem cell niche). In particular, a synthetic niche is surrounded by an external perimeter that is permeable to the diffusion of molecules but obstacles the migration of cells from a synthetic niche to the adjacent ones (physical confinement). "Nichoid", as a synonym of synthetic niche, will also be used in the foregoing of the present description. For an exemplary description of a synthetic niche, reference can be made to the articles by Raimondi et al, 2014, in Micromachines, and 2013, in Acta Biomaterialia.

In the context of the present invention, the term stem cells mean primitive, unspecialized cells being able to transform into various types of body cells through a process known as cellular differentiation.

In the context of the present invention, the term mesenchymal stem cells mean adult stem cells found in bone marrow that can differentiate into every type of musculoskeletal tissue cell, including osteocytes, chondrocytes, myocytes, and fibroblasts.

In the context of the present invention, the term pluripotent stem cell mean cells that are capable of dividing and differentiating into any one of three germ layers: endodermal (stomach lining, gastrointestinal tract, lung), mesodermal (muscle, bone, blood, urogenital), or ectodermal (epidermal tissue and nervous system cells).

In the context of the present invention, the term multipotent stem cells mean cells capable of differentiating into a limited number of cellular lineages; these cells are also known as «progenitor cells».

FIGURES

FIG. 1. Exemplary representation of a supermatrix according to the invention characterized by matrices of 5×5 synthetic niches, separated by a distance d.

Figure 2:
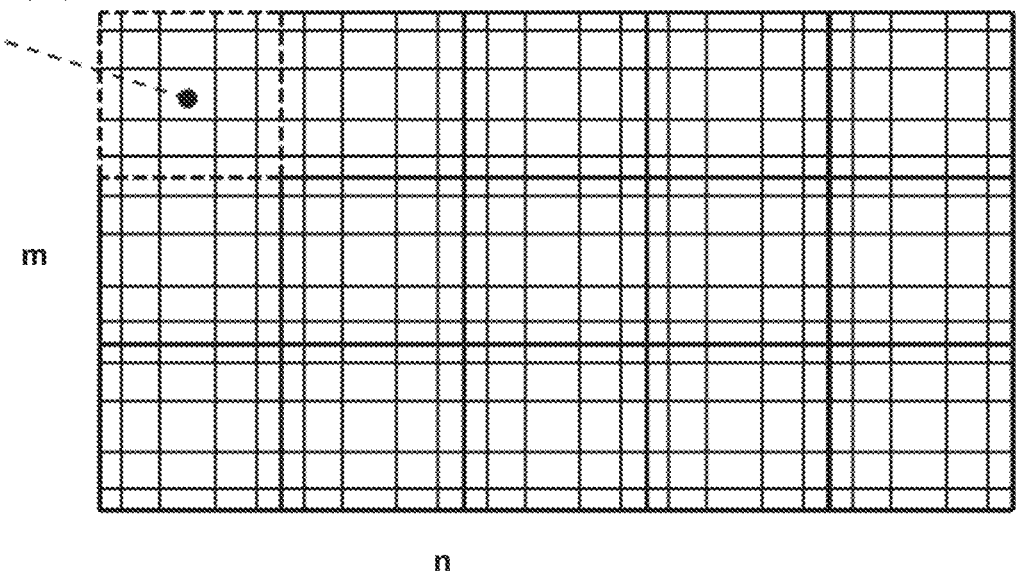

FIG. 2. Exemplary embodiment of a matrix formed by 15 synthetic niches, wherein n=5 and m=3.

Figure 3:
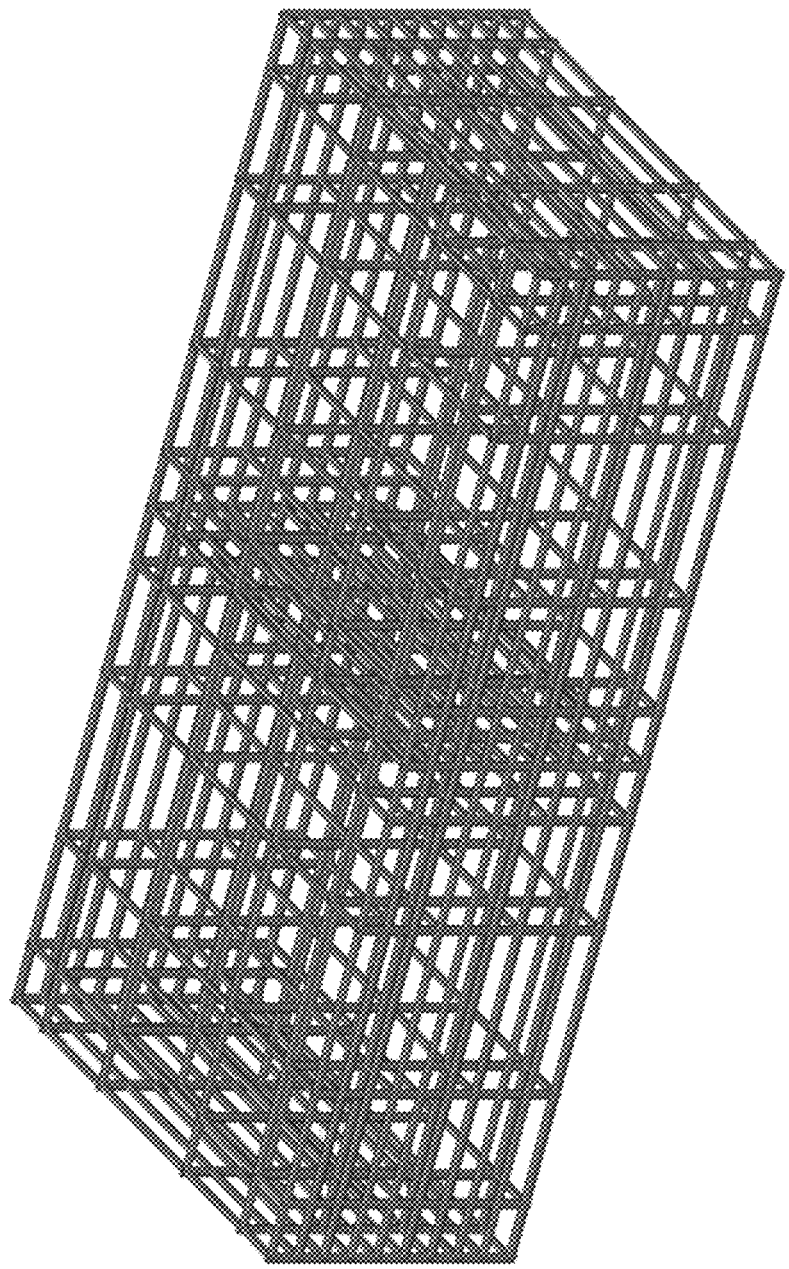

FIG. 3: minimum matrix (2×1).

FIG. 4. (A) Supermatrix that shows problems linked to microfabrication. (B) Effect of shrinking, with deformation of the structure; (C) Effect of cavitation; (D) Exemplary embodiment of the supermatrix according to the invention, characterized by separate matrix configuration. The aggregates visible are murine embryonic stem (mES) cells at culture day 3.

FIG. 5. Photos by optical microscope (A) and SEM (B) of an exemplary embodiment of the supermatrix according to the invention.

Figure 6:
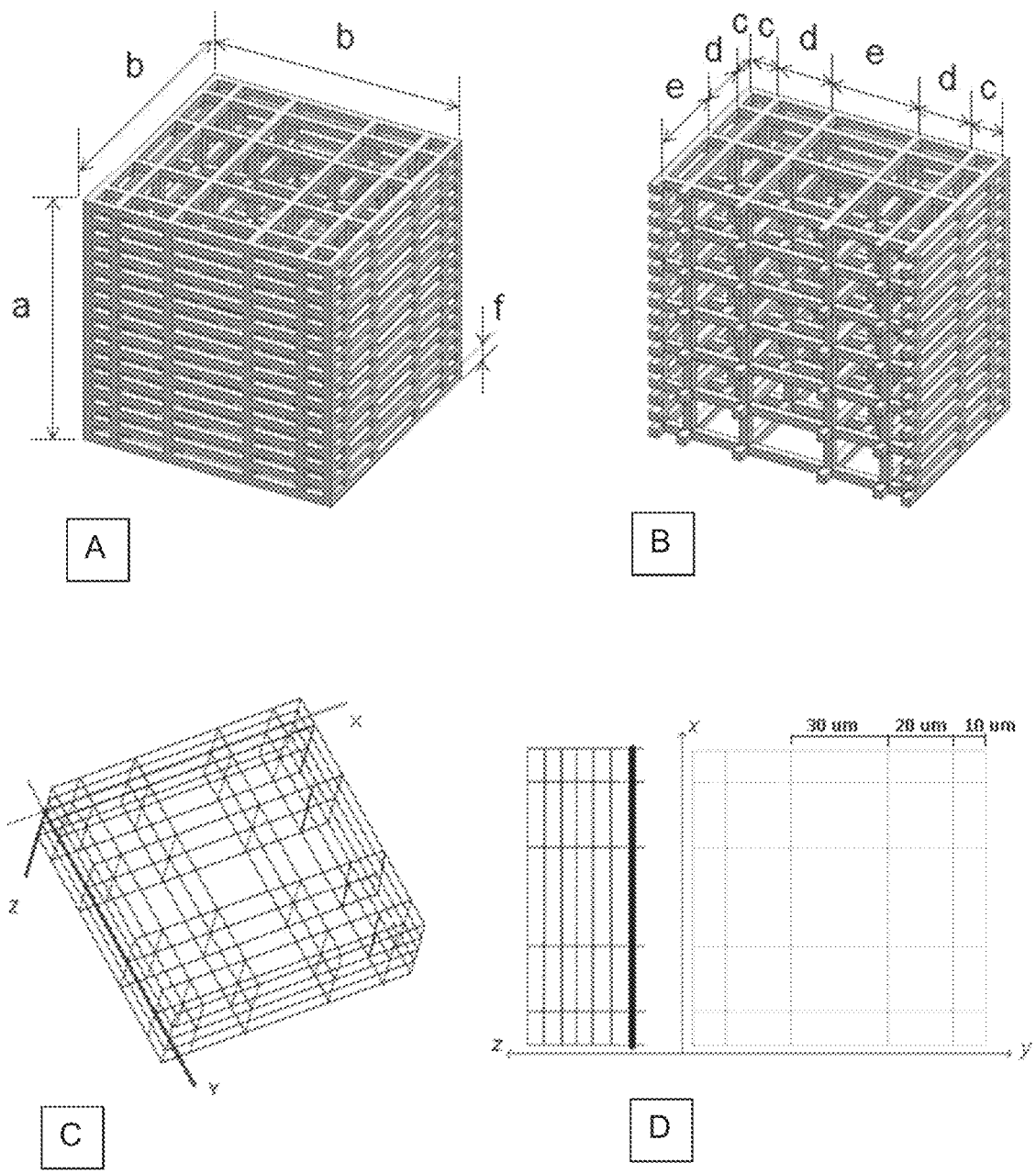

FIG. 6. A-B) Exemplary embodiment of a synthetic niche used in a supermatrix according to the invention, complete (A) and sectional view (B). The niche is a parallelepiped, formed by an external containment grid made of horizontal parallel lines, identically spaced, and by an internal 3D lattice of variable geometry and size. Lattice structure wherein a=100 μm, c=10 μm, d=2c and e=3c. The parallel lines in the walls are spaced by f=5 µm. C-D) Graphic representation of how single niches are designed.

FIG. 7: Optical microscope photo of an exemplary embodiment of single niches: each scaffold lies 300 µm from the next.

Figure 8:
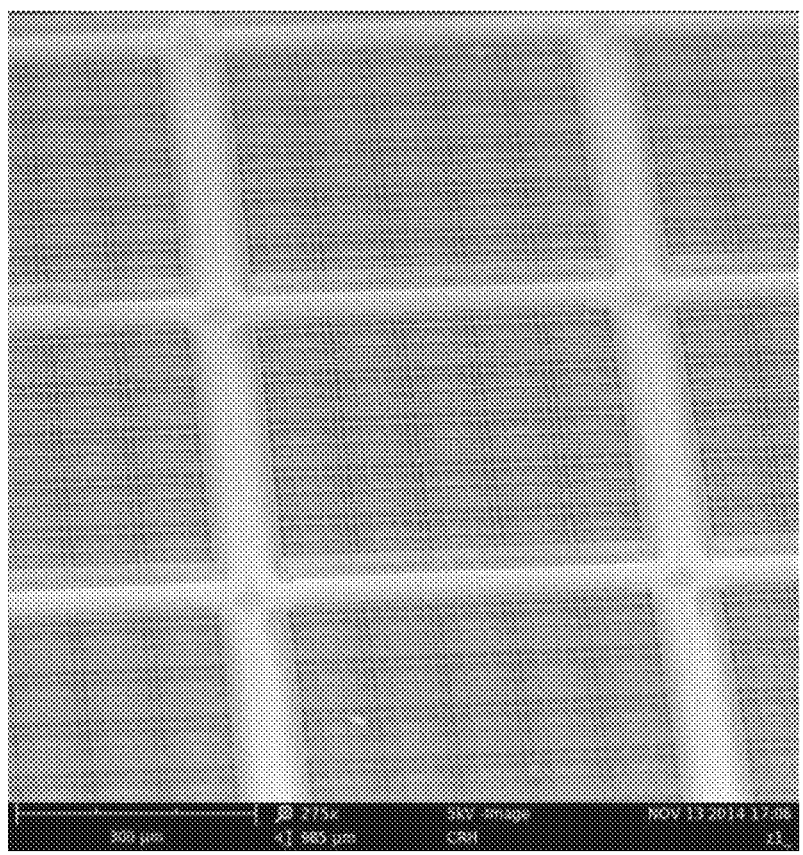

FIG. 8: SEM microscope photo of an exemplary embodiment of a supermatrix formed by 5×5 synthetic niche matrices.

Figure 9:
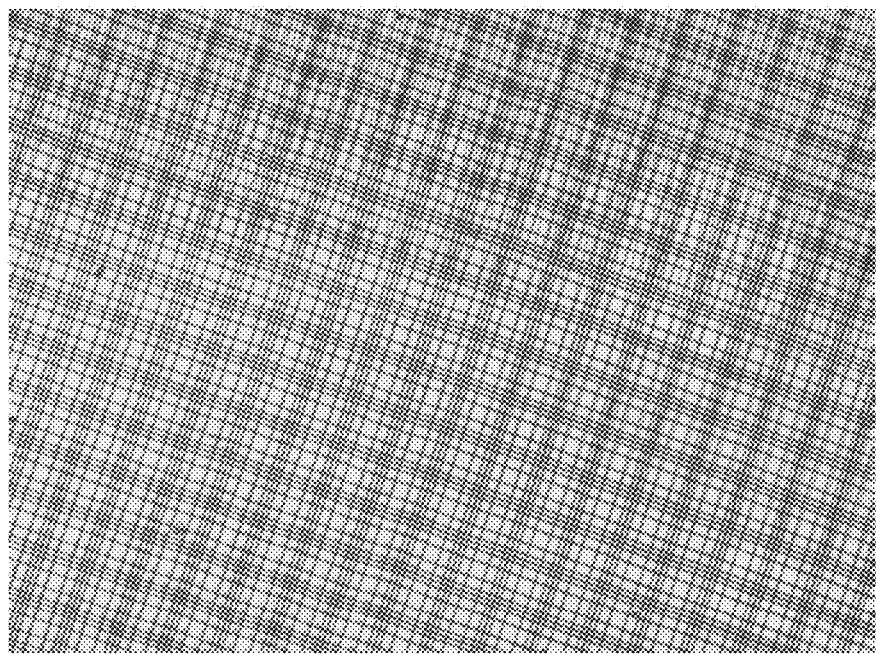

FIG. 9: Optical microscope photo of an exemplary embodiment of a series of synthetic niches in which a continuous lattice produced by the pairing of single niches entirely covers a region, with damages caused by the shrinkage (contraction) of the polymer during the "development" phase of fabrication.

Figure 10:
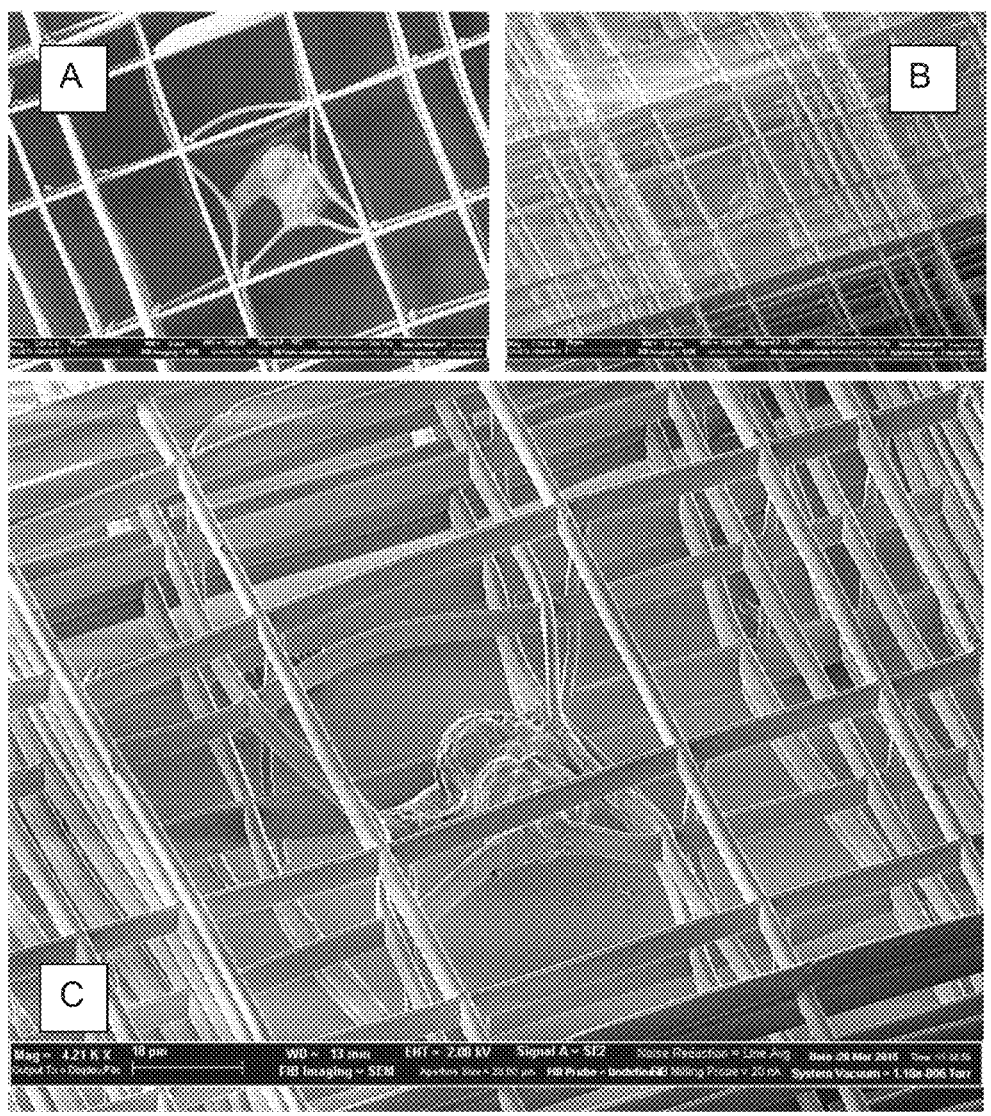

FIG. 10: mES inside a niche. SEM microscope photo of mES cells at culture day 3. All three photos show the same region but were acquired from different angles. (A) top view (Tilt 0°), the way in which a cell aggregate, so-called embryoid body, adheres tightly to the structures is clearly evident: structure deformation is almost certainly due to cellular shrinkage during the dehydration phase because in vivo, under phase contrast microscopy, a similar deformation has never been observed. (B) Tilt 30°. (C) Detail of the photo taken with Tilt 30°: the embryoid body adheres to the intermediate niche level on the front side, whereas it adheres to the base level on the rear side; the embryoid body does therefore not rest on the bottom surface of the culture support, as normally happens in 2D flat supports.

FIGS. 11.1-11.4. Computerized simulation of the laser writing of an exemplary embodiment of the supermatrix according to the invention.

Figure 12:
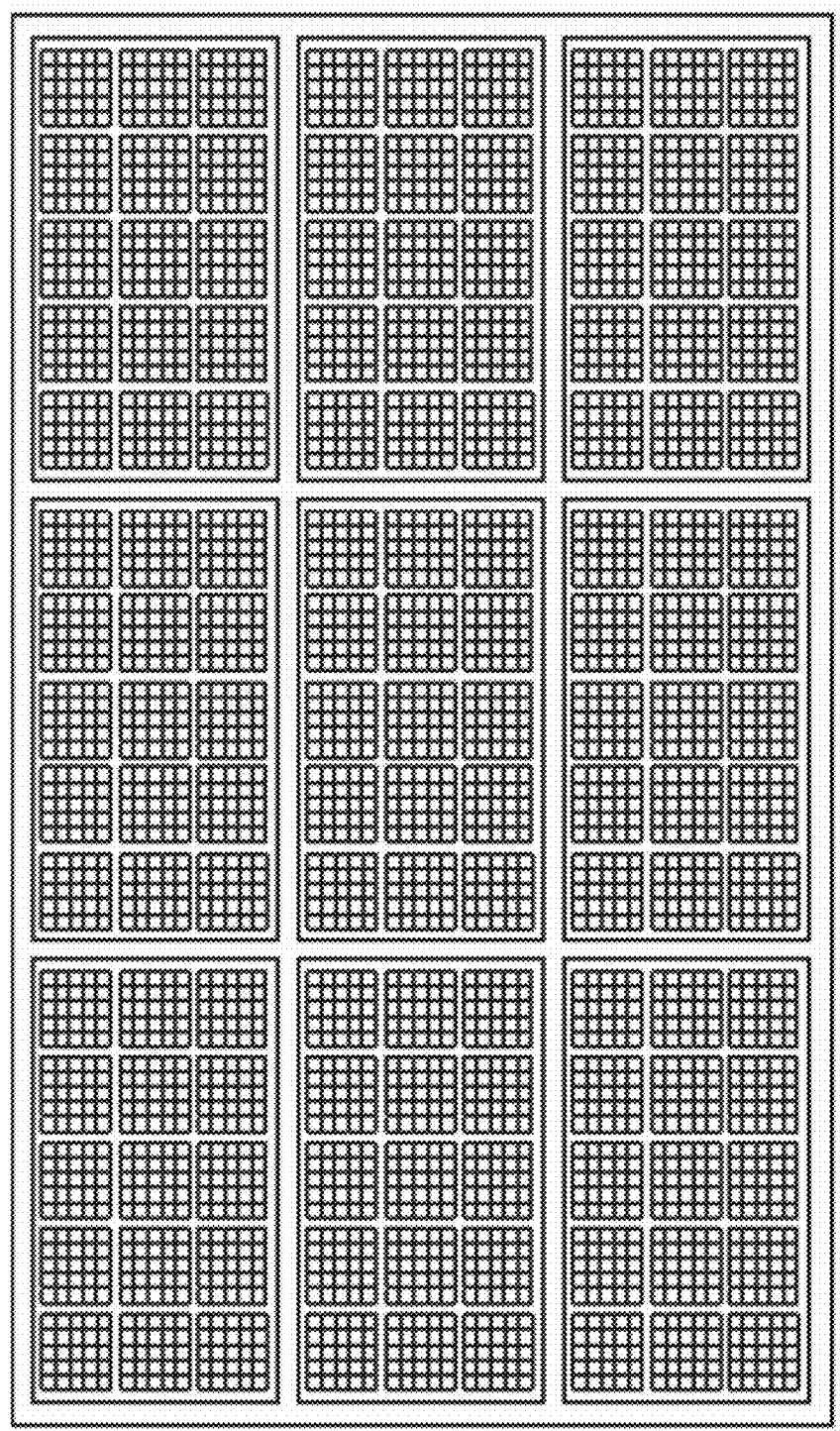

FIG. 12: exemplary representation of a multi-well culture plate coated with the supermatrices of the invention.

The supermatrix according to the invention is formed of matrices of synthetic niches.

One embodiment of the supermatrix according to the invention is depicted in FIG. 1.

Each matrix is formed by a certain number n×m of synthetic niches.

In each matrix, each synthetic niche has one or more walls in common with the other(s) synthetic niche(s) of the matrix.

In a preferred embodiment, each synthetic niche of the matrix has two or more walls in common with the other synthetic niches of the matrix.

An exemplary embodiment of a matrix of synthetic niches is depicted in FIG. 2.

The matrix can have various shapes. In one preferred embodiment, it has a square shape.

In the matrix m and n have a value ≥1, provided that at least one of m or n is ≥2.

Therefore, the minimum matrix is a 2×1 matrix, as shown in FIG. 3. In this minimum matrix each niche has one wall in common with the other niche.

The maximum value of m and n is the one that permits to obtain a matrix without ruptures or deformations such to compromise the stability of the supermatrix. This can be easily evaluated by a person skilled in the art with the knowledge of the techniques commonly known in the sector, in particular for niche fabrication.

For example this maximum value for m and n equals 100.

The distance between one synthetic niche matrix and the next is defined by the value d.

Said distance d is always greater than zero, therefore the matrices are necessarily spaced one from another.

Preferably, said distance is the minimum obtainable using today's fabrication techniques.

The structure of a single synthetic niche is known, for example by Raimondi et al. 2014 and 2013.

In a preferred embodiment (FIG. 6), every single synthetic niche has a square section with 90 µm sides (b), 100 µm height (a), and having 6 stacked layers of lattices. In every lattice, the pores have dimensions that vary between 10 µm and 30 µm. Confinement walls around the niche's perimeter, made of parallel rods at a distance of 5 µm (f) one from the next, are also provided. The rods of the niche protrude for around one micron beyond the structure.

The dimensions of the single niche may vary according to the specific type of cell being cultured, while always maintaining three-dimensional structure. A person skilled in the art can determine the modifications to be made to the niche on the basis of cell type.

For example, the width and depth of the niche may vary between 20 and 500 µm with pores that vary from 5 to 100 µm, preferably from 10 µm to 30 µm. Height may vary from 5 to 500 µm, preferably from 30 µm to 100 µm. Each niche can have several layers of lattices, for example from 2 to 10 layers, preferably from 4 to 6 layers. Confinement walls are preferably made of parallel rods at a distance one from the other which may vary, for example, from 2 to 30 µm, preferably from 2 to 10 µm, more preferably it is 5 µm.

In a preferred embodiment, the height of the supermatrix is 30 µm, in particular, whenever it is used for mesenchymal stem cell culture. Said height permits all known microscopy techniques for cellular analysis to be applied to the cells that grow in the niches.

In case highly proliferative stem cells are cultured, such as pluripotent stem cells (e.g. embryonic) a height of more than 30 µm is preferable.

The supermatrices according to the invention are typically fabricated over a flat support.

Said flat support is typically made of a material optically transparent to the two-photon laser, preferably glass or a polymer, for example of the polyolefin family.

In one embodiment of the invention, the flat support on which the supermatrices of niches are fabricated is chemically or physically modified for the purpose of minimizing cell adhesion to the support areas outside and below the area in which 3D structures are present. In a preferred embodiment, the flat culture support is coated with an agent that reduces the wettability of the cell culture surface, for example by an antifouling agent such as perfluoropolyether.

Optionally, the supermatrices according to the invention are surrounded by a circular crown of Polydimethylsiloxane (PDMS) or equivalent material characterized by elevated biocompatibility and stability. PDMS is produced through known art in the sector by mixing two different components: a base and a cross-linking agent in a 10:1 weight ratio, in such way as to permit polymerization. PDMS obstructs both physically and chemically the adhesion of the cells outside the area in which 3D structures are present.

Optionally, the walls of the niches of the supermatrix are functionalized with molecules.

In a preferred embodiment, these molecules provide an inductive signal for pluripotency maintenance or facilitate the adhesion of the cells to the structure.

In one embodiment of the invention, each niche in the structure can be coated with appropriate substances or molecules, ad example for the purpose of modifying the response of the cells cultured. For example, each niche can be coated with hyaluron-based and gelatin-based hydrogels in order to simulate a different elasticity in the cellular matrix, as described in an article published by Nava et al. in 2015.

The supermatrix according to the invention is fabricated using the known technique of two-photon laser polymerization.

As regards the use of said technique to produce synthetic niches, reference can be made to the following works: Raimondi M T, Eaton S M, Nava M M, Laganà M, Cerullo G, Osellame R. Two-photon laser polymerization: from fundamentals to biomedical application in tissue engineering and regenerative medicine. J Appl Biomater Funct Mater. 2012 Jun. 26; 10(1):55-65; Raimondi et al., 2013, and Raimondi et al., 2014, both previously mentioned above.

The specific protocols for the production of a supermatrix according to the invention may vary on the basis of the type of cell that is cultured. A expert in the field is capable of defining such technical specifications on the basis of his general knowledge in the field.

For example, regarding the culturing of mesenchymal stem cells, reference can be made to the work published by Raimondi et al in 2013.

An exemplary embodiment of the process to obtain a supermatrix according to the invention is described below.

The material utilized for production is a resin. Preferably, it is a photopolymerizable resin. Said resin is typically an organic/inorganic hybrid photosensitive material that polymerizes when it is illuminated by laser. In this regard, reference can be made, for example, to an article by Raimondi M T, Eaton S M, Nava M M, Laganà M, Cerullo G, Osellame R. Two-photon laser polymerization: from fundamentals to biomedical application in tissue engineering and regenerative medicine. J Appl Biomater Funct Mater. 2012 Jun. 26; 10(1):55-65.

Preferably, the resin is a photopolymerizable resin known as SZ2080. This resin is known (Ovsianikov A, Viertl J, Chichkov B, Oubaha M, MacCraith B, Sakellari I, et al. Ultra-low shrinkage hybrid photosensitive material for two-photon polymerization micro-fabrication. ACS Nano 2008; 2:2257-62) and has been developed recently. Its use is preferable thanks to its good optical qualities and mechanical stability. The two main components of SZ2080 are meth acrylol oxypropyl trimethoxy silane (MAPTMS) and zirconium propoxide (ZPO). The resin's index of refraction can be modified by varying the molar ratio between these two components, and increases proportionally with the increase in ZPO.

The supermatrix production process comprises three principal phases: baking, laser writing, and development.

During the baking phase, the samples are prepared by hardening the above-mentioned resin.

A photoinitiator must be incorporated into the resin in order to permit two-photon absorption. One preferred photoinitiator is IRG (Irgacure 369,2-Benzyl-2-dimethyl-1-(4-morpholinophenyl)-butanone-1), which is not cytotoxic. Another possible photoinitiator is BIS (4-4'bis(diethylamine) benzophenone).

Both the specific chemical properties of the resin and the geometry of the scaffold that supports the supermatrix must be taken into consideration.

The resin and photoinitiator solution is deposited by dropcasting, for example, in a volume that varies from 30 to 50 μL, onto the support on which the supermatrix must be obtained, such as a coverglass, for example, or directly inside multi-well culture plates in which the cells will be seeded.

The sample is then positioned on a plate. This process (baking) is necessary for the solidification of the resin on the glass substrate and to ensure that the solvents in which it is dissolved evaporate. In this way, its consistency changes from liquid to semi-solid.

The sample then undergoes the writing process.

The sample is usually positioned in a special housing chamber connected to a motion system composed of a piezoelectric position transducer controlled by software.

An ultra-short pulsed laser system is used for writing. Any laser commonly used in 2PP technique can be utilized. For example, reference can be made to Raimondi et al., 2013.

For example, a commercially-available laser can be used, such as the Femtoregen model produced by the HighQ Company, a model based on a mode-locked Ytterbium (Yb) oscillator followed by an amplifier.

The laser typically has a pulse duration in the range of 10 fs and 10 ps, and a wavelength in the range of 400 and 1300 nm.

Preferably, the laser is used at a power in the range of 12 and 21 mW and at a writing speed of 1000 μm/s.

Stages that permit the translation of the sample mounted on a sample-holder that is solidly connected with the 3D movement system are used to permit complex geometries to be written in the resin.

Movement commands are given by software via G-code, a language commonly used in numerically controlled machine tools.

In one embodiment of the present invention, the software program is written in such way as to fill the circular surface area defined in the parameters with all the rods first; then, all the lattices on the different levels are written, first in one direction then the other before finishing the process with the confinement walls that enclose every single structure. The supermatrix is obtained by programming the software in such way as to write a series of niche matrices, with the limitation of writing only inside one-quarter of a circle, and then repeating it in all four directions in order to complete the surface. See FIGS. 11.3 and 11.4., for example.

The movement of the sample compared to that of the laser beam can be programmed using a Computer-Aided Design (CAD)/Computer Aided Machining(CAM) system or the joint and integrated use of software systems for, CAD, and CAM.

Each component of the system can be managed by personal computer (PC).

A person skilled in the art is able to compile the various software that permit the laser writing to be set in accordance with the fabrication desired and the general knowledge in the field.

After the writing phase, the sample undergoes the development phase, i.e. the elimination of the fraction of non-polymerized resin.

Development typically takes place by immersing the sample in a development solution selected on the basis of the photosensitive resin used. For example, a 50:50 isopropanol and pentanone solution can be used for around 10-15 minutes (duration depends on the quantity of material used and the complexity of the structures created).

The supports thus obtained can be used for cell culture.

Prior to use, they are preferably sterilized using known methods in the sector; see for example Raimondi et al. 2014.

The seeding of the support with the cells to be cultured can be performed using known techniques in the sector. On the basis of this general knowledge, a person skilled in the art is able to adjust the timing and the other parameters required for cell culture.

For example, for mesenchymal stem cell culture, reference can be made to Raimondi et al., 2013.

The supermatrix according to the invention can be advantageously used in a wide-scale cell culture system with ample industrial and commercial applications.

Preferably, said supermatrix is used to coat the bottom of a culture well, said well that is part, for example, of a mono- or a multi-well culture plate.

An exemplary embodiment of a multi-well culture plate whose bottom is coated with supermatrices of synthetic niches according to the invention is depicted in FIG. 12.

Optionally, the surface of the culture plate can be functionalized with suitable molecules before being coated with the supermatrices. For example, it can be chemically or physically modified for the purpose of minimizing cell adhesion to the support areas outside and below the area in which 3D structures are present. In a preferred embodiment, the culture plate is coated with an agent that reduces the wettability of the cell culture surface, for example it is coated with an antifouling agent such as perfluoropolyether.

The supports containing the supermatrices according to the invention can be used for any type of cell culture that requires a three-dimensional structure in order to increase the volume occupied by the cells.

In a preferred embodiment, the supports containing the supermatrices according to the invention are used for stem cell culture.

Said stem cells can be multipotent or pluripotent.

More in particular, these can be natural pluripotent cells, such as embryonic stem cells or induced pluripotent cells, i.e. adult somatic cells that are made to regress to pluripotent stem cells through genetic engineering techniques.

Preferably, these are adult stem cells, i.e. stem cells that are present in human adults. Adult stem cells can be taken from different types of adult organism tissue, such as umbilical cord, amniotic sac, blood, bone marrow, placenta, and adipose tissue.

The use of the supermatrices according to the invention for the culture of mesenchymal stem cells is particularly preferred. These can be taken, for example, from the bone marrow or other parts of the body, such as the umbilical cord or adipose tissue, of adult donor volunteers.

Any cell culture support that comprises the supermatrix described herein is within the scope of the present invention.

Cells cultured on the supermatrices of the invention can be used on wide scale in regenerative medicine or for the production of tissues to be implanted in vivo.

Also, they can be used as a therapeutic product to modulate inflammation in degenerative diseases or to avoid immune-rejection in organ transplantation.

For example, once a critical number of cells has been obtained, they can be made to differentiate or kept undifferentiated, as required by therapeutic need, and then injected into a patient to treat currently incurable diseases, such as Parkinson's disease, for example.

Also the elements secreted by said cultured cells, which are known as "secretomes", can be used as therapeutic products, for example in the treatment of degenerative diseases.

For example, the above-mentioned critical number of cells can be suspended in culture for the purpose of producing a high quantity of "secretome" that can be injected in patients on repetitive basis, for example in order to reduce inflammatory response in degenerative diseases such as Crohn's disease, arthrosis, rheumatoid arthritis, and Alzheimer's disease.

The supermatrices according to the invention are also useful as laboratory tools and in wide-scale biological research thanks to the possibility to culture a high number of stem cells to be kept undifferentiated for use in substrate for cellular analysis.

Lastly, supermatrices according to the invention can also be used as 3D supports to be implanted in vivo in a subject for the purpose of promoting the regeneration of tissue or an organ through cellular and micro-vascular re-population. This can be done using methods commonly known in the field.

The invention is further illustrated by the following examples.

EXAMPLES

Example 1: Micro-Fabrication of the Nichoid Matrix for Stem Cells

Materials and Methods

A SZ2080 photoresist with the Irg photoinitiator selected for its greatly reduced auto-fluorescence, was used to fabricate the niches by means of 2PP. In order to prepare the sample prior to writing, baking had to be performed in order to solidify the photoresist (at 105° C. for 1 hour). The experimental setup used for fabrication included: a Yb-based writing femtosecond laser, a mechanical shutter, a power control, and an objective lens. The pulses of the femtosecond laser passed first through a power control consisting of a birefringent plate followed by a linear polarizer. The pulses were then focused using an objective lens inside the photoresist, and the position of the sample compared to that of the beam was shifted with the use of a computer-controlled 3-axis motion stage.

In order to study the effect of the niches on stem cell fate, first 10% and then up to 88% of a circular surface (see FIG. 7 and FIG. 8 respectively) were coated with niches.

The software program for niche fabrication was written in G-code in order to fill the circular surface defined in the parameters with all the rods first (FIG. 11.1), and then all the lattices on the different levels, first in one direction then the other (FIG. 11.2) before finishing the process with the confinement walls that enclose every single structure.

The nichoid supermatrix was fabricated by programming a series of niches, with the limitation of writing only inside one-quarter of a circle (FIG. 11.3), and then repeating it in all four directions in order to complete the coverglass (FIG. 11.4).

After laser writing, the samples were immersed in a 50:50 solution of isopropanol and pentanone in such way as to eliminate the non-polymerized part of the photoresist. The niches were observed through optical and SEM microscope and then surrounded with a circular crown of Polydimethylsiloxane (PDMS) in order to obtain a non-fouling surface for the cells around the circular area coated with niches. This circular crown is not essential for the fabrication of the supermatrix according to the invention.

Biological and functional analyses were performed through a series of standard tests (clonogenic, cell function, and immunofluorescence assays) in order to test MSC pluripotency maintenance.

Biological Validation of Single Niches Using Human MSC

Studies were conducted on MSC derived from human bone marrow (hBM) cultured for three weeks on the synthetic niche substrate. The morphology, proliferation, and clonogenicity of the cells cultured on the niches were analyzed in order to demonstrate multipotency maintenance compared to both cells cultured on control structures (flat glass substrates) and to cells isolated and cryo-preserved from passage 0 to the moment of use (cells P0).

Lastly, for the purpose of verifying cell multipotency maintenance, after 3 weeks of culture, immunofluorescence for the CD146 marker, one of the possible multipotency markers, was analyzed using fluorescence-activated cell sorting (FACS). Real-Time Polymerase Chain Reaction (RT-PCR) was used to analyze the expression of a group of genes involved in MSC osteogenic commitment, which is the spontaneous fate of hBM-MSC in vitro (P-C. Tseng, T-H. Young, T.-M. Wang, H-W. Peng, S-M. Hou, and M-L. Yen. Spontaneous osteogenesis of MSC cultured on 3D microcarriers through alteration of cytoskeletal tension. Biomaterials, 33(2):556-564, 2012).

Cell Isolation and Culture Protocol

Bone marrow was taken from 2 healthy donors aged 18 and 65 respectively during routine orthopedic surgery procedures with the consent of the local ethics boards (Basel University hospital) after first obtaining informed donor consent. The bone marrow aspirate was deposited in a standard flask and cultured for a week in α-MEM with the addition of 20% FCS, 1% sodium pyruvate, 1% PSG (penicillin G and 0.1 mg/mL streptomycin) and 1% HEPES. The culture medium was changed regularly twice a weeks until confluence. The MSC were recovered from the bone marrow by taking advantage of their tendency to adhere tightly to culture plates, whereas the other non-adhering cells were removed. Adherent cells were detached by trypsin-EDTA (0.5-0.2 g/L; Invitrogen, Carlsbad, Calif., USA), counted, and cryo-preserved in α-MEM supplemented with 30% FCS and 5% dimethyl sulfoxide (DMSO) until use. The 2PP-patterned coverglasses (referred to below simply as 2PP samples) were washed thoroughly, kept for 12 hours in deionized water, disinfected for 12 hours in ethanol at 7%, washed repeatedly in sterile deionized water, and then UV-sterilized. Each sample was positioned in an Ultra-Low Attachment 24-well cell culture plate (Costar 3473, Corning, Corning, N.Y., United States of America). The cryo-preserved cells were resuscitated, suspended in complete medium and seeded directly in the wells at a density of 10,000 cells/cm$^2$. The cells were incubated for 21 days with medium freshly replaced twice a week.

As regards biological analysis, after 3 weeks of culture, the cells were detached using trypsin-EDTA and counted for the purpose of conducting the analysis below.

Biological Analysis, Immunofluorescence, and RT-PCR

Morphological analysis was performed under a standard microscope (IX50, Olympus, Tokyo, Japan) equipped with a cooled high resolution video camera. In order to assess clonogenicity (the capacity of cells to form colonies), after three weeks of culture in the sample 2PP structures, the cells were detached, counted, and reseeded in triplicate in Petri plates. In each plate, 600 cells were cultured in complete medium changed twice weekly. After 2 weeks of culture, the cells were washed in PBS, fixed with 3.7% paraformaldehyde in PBS and stained with Crystal Violet for 10 minutes. The dye was then collected and the plates were washed with water and left to dry. Clonogenicity capacity was calculated as the percentage between the number of colonies counted manually and the number of cells seeded. The number of clonogenic cells (i.e the cells capable of forming colonies, CFU) was calculated as the product of the total number of cells trypsinized after 3 weeks of culture and the clonogenicity capacity percentage.

In order to perform real-time PCR, the total RNA was extracted from the cells using TRIzol (Invitrogen, Carlsbad, Calif.), treated with DNA-asi and reverse transcribed in cDNA as per standard procedure. Real-time PCR was performed using the ABIPrism 77000 Sequence Detection System (Perkin Elmer/Applied Biosystem, Rotkreuz, Svizzera), and the levels of expression of the genes of interest RUNX2, Bone SialoProtein (BSP) and PPAR-gamma were normalized for the reference gene GAPDH. This gene is, in fact, the one that is actively transcribed and translated at relatively high level.

For FACS analysis, cells cultured in the sample 2PP structures for three weeks were re-suspended in 200 μl of BSA at 0.5% in PBS (FACS buffer) with antibodies bonded with fluorochromes for the protein in question. The antibodies were incubated for 30 minutes at 4° C. The antibodies used were CD146-PE and IgG1-PE (Becton, Dickinson and Company, Franklin Lakes, N.J.). All the antibodies were used with 1:50 dilution. The cells were washed 2 times with FACS buffer, re-suspended in PBS, and analyzed by FACS (Becton, Dickinson and Company).

In order to perform fluorescence analysis and examination by confocal microscope, the cells were fixed in 2% paraformaldehyde, permeabilized with 0.2% Triton, blocked with 2% goat serum albumin (GSA) in PBS, and fluorescently marked. The DNA was stained by incubation with 4',6'-diamidino-2-phenylindoledihydrochloride (DAPI) in solution at 10 μg/ml. A secondary antibody (Alexa Fluor 566 nm) was used to identify the integrin of the membrane CD146.

Image acquisition and 3D reconstruction were performed at 20× and 60× using a confocal laser microscope (Nikon A1R, Japan).

Adipogenic assays were conducted using standard protocol (A. Barbero, S. Ploegert, M. Heberer, and I. Martin. Plasticity of clonal populations of dedifferentiated adult human articular chondrocytes. Arthritis Rheum, 48(5):1315-1325, 2003).

Also osteogenic assays were conducted using the standard protocol described in literature (N. Jaiswal, S. E. Haynesworth, A. I. Caplan, and S. P. Bruder. Osteogenic differentiation of purified, culture-expanded human mesenchymal stem cells in vitro. J Cell Biochem, 64(2):295-312, 1997).

Results

Results of Fabrication

We were able to confirm that the best configuration possible to coat the circular surface of the coverglass with single niches positioned at regular distances from one another is the one that leads to the obtainment of a hexagonal pattern.

After developing a procedure that permitted the fabrication of engineered niches, the area effectively occupied by the niches in relation to the total area seeded was quantitatively verified. A geometric analysis showed that the area covered by niches spaced 300 μm apart was only 10%, whereas the area increased dramatically when the niches were spaced only 200 μm or even 100 μm apart.

An attempt at completely eliminating the distance between one single niche and another was made by creating one single matrix of niches, in which the same type of niche was repeated but with shared walls, and therefore many more niches filled the entire coverglass. As many as 1484 niches were made in a matrix with 2 mm radius (M2) and 3396 niches in a matrix with 3 mm radius (M3). In this way, up to 97% of the area available can be covered (not 100%, because a perfect circle is not drawn and a graded configuration remains at the edges).

Unfortunately, not all the niches were acceptable because for various reasons they tend to deteriorate during the development phase of fabrication, sag under their own weight, detach, or simply not maintain the stable linear geometry imposed on them by the software.

The matrices M2 and M3 presented the problem of the shrinkage of the polymer during expansion (FIG. 9), that caused mechanical stress and deformation, which provided the reason for dividing the structure in smaller matrices (for example of 450 µm in side, spaced 20 µm apart). The excessive dimensions of the surface covered by the structures risked damaging certain parts of the niche, with repercussions throughout the rest of the structure.

By separating the bigger matrix into smaller matrices, instead, the slight shrinkage of the polymer does not ruin the entire structure and furthermore such shrinkage is not added to the shrinkage in adjacent areas. This led to the need to create a supermatrix made of smaller matrices of synthetic niches, capable of providing effectively more solid and stable three-dimensional structures without deformation and in which all three stacked levels of the niches were present (FIG. 5A-B). This conformation is the only one that provided repeatable engineered niches for most of the sample structures developed.

The attempt to extend the coated surface area to 100% of the coverglasses was abandoned because the excessive dimensions of the structures fabricated caused the shrinkage of the polymer with structural deformation and instability as a result.

Results of MSC Culture in Single, Up-Scaled Niches

One of the most significant findings of biological analysis is that no formation of aggregates between niches was observed. Average cellular density was statistically greater than 67% in the niches than in glass surfaces.

After the dimensions have been established and structurally stable niches have been obtained, the vitality and adhesion of the cells to their interiors can be analyzed and their proliferation, differentiation, and migration can be observed. Previous studies had reported that during the proliferation phase cells are concentrated in highest number in the central areas of the colonies, and in particular, in the interior volume of the niches and on their external walls. The morphology of human MSC derived from bone marrow cultured in sample structures obtained through 2PP technique was assessed on the basis of these previous results.

Stem cells seeded on niches were observed to proliferate on both the flat surface of the glass that surrounds them and inside the same. Contrary to what observed inside the niches, no formation of cell aggregates was observed on the surrounding glass.

After 3 weeks of culture the cells were counted for every culture condition tested.

It is possible to state that niches provide stem cells with an increase in the surface area/volume ratio that favors their adhesion and allows much more space for proliferation.

For this reason, the synthetic niche system is capable of guiding aggregate formation even with hBM-MSC cells. This spontaneous tendency to form aggregates is not species-specific. Differences in cell density values, on the contrary, may instead be species-specific.

Clonogenic assays were performed on cells cultured on both 2PP sample structures and on glass substrate samples. Even if no statistical significance was observed, a higher average number of cells maintained clonogenic in 2PP samples than on glass. Compared with cells cultured on glass substrates, cells expanded on 2PP substrates showed a significantly greater colony diameter, which is an index of clonogenic potential.

Following medium conditioning on 2PP-cultured cells, the expression of RUNX2 and BSP genes, as well as PPAR-gamma, was significantly greater than that measured on glass controls.

In conclusion, human MSC expanded on the synthetic niche substrate maintained their proliferative potential, clonogenic capacity and bilineage differentiation potential more effectively than cells expanded on glass substrates and in some aspects were comparable to non-expanded cells.

CONCLUSIONS

The extension of the culture surface covered by single niches to 10% of the culture surface proved to be fundamentally important to achieve a greater number of cells for the analyses, although the contribution from areas without niches conditioned the experimental results. It can be stated that niches can guide the formation of aggregates while maintaining MSC proliferative potential and multipotency more effectively than 2D surfaces.

Therefore the niches, and in a particularly advantageous way the extended substrate, can be used for the culture and expansion of undifferentiated MSC.

Once a critical number of cells has been obtained, they can be conditioned to differentiate or maintained undifferentiated as required by the needs of treatment, and then injected into a patient to treat presently incurable diseases, such as Parkinson's disease, for example.

The artificial niche substrate permits a reduction of the effects of 2D surfaces that affects biological results. This demonstrates that 3D geometry and the consequent method of cellular adhesion is an important source of stimulation, perhaps the most important, in determining the maintenance of MSC multipotency.

Example 2

Quantification of the Effect of the Nichoid Supermatrix on the Pluripotency of Embryonic Stem Cells without Chemical Conditioning Materials and Methods Cells The experiments on the nichoid supermatrix were conducted using murine embryonic stem cells (mESc). Not adhesion-dependent, these cells are highly clonogenic and characterized by their reduced size (10 µm diameter) caused by a limited cytoplasmic region, in this way promoting perfect homing inside the engineered niches. The mESc utilized are a part of the R1 line and were obtained from Nagy Lab at Mount Sinai Institute, Toronto, Canada. The in vitro cell cultures were kept in a controlled-atmosphere incubator at 37° C. with 5% $CO_2$ and 95% relative humidity. The culture medium was composed as follows: DMEM (Gibco, 11960), 10% decomplemented FBS (Gibco, 16141), 1% L-Glutamine (Invitrogen, 25030024), 1% non-essential amino acids (Invitrogen, 11140035), 1% sodium pyruvate (Gibco, 11360), 1% Penicillin-Streptomycin (Invitrogen, 15140122), 0.1% β-mercaptoethanol 0.1 mM (Sigma M7522) e 1000 U/ml LIF (Millipore, ESG1107). The maintenance of the line was promoted by the presence of feeder cells: here, primary CD1 mouse embryonic fibroblasts were used after being treated in p3 with mitomycin-C(Roche, 10107409001), an alkylating agent that induces the formation of a cross-link at DNA level, in this way preventing duplication and therefore cellular proliferation. This treatment is essential in order to enable precise control of the density of these cells in culture. The expansion of the mouse embryonic fibroblasts (MEF) up to p3 was conducted in a specific medium composed of DMEM, 10% FBS, 1% Penicillin-Streptomycin and 1% non-essential amino acids. After being isolated from the animal and treated with mitomycin, they were plated in flasks (Corning, USA) and pre-treated with 0.1% porcine gelatin with density varying from between $6.5$-$10.5 \cdot 10^3$ cells/cm$^2$: Generally speaking, if the line is stable, mESc are seeded on MEF with $26.5 \cdot 10^3$ cell/cm$^2$ density (or more simply, two million in a T75). The medium was changed every two days until confluence was reached. The detachment process consisted of an initial incubation phase with trypsin (0.05% in medium R1) at 37° C. for 3 minutes, a second centrifugation step at 1200 rpm for 5 minutes, and lastly, the re-suspension of the pellet in complete R1 medium (R1+LIF) followed by new seeding in flask in the presence of MEF. Cryo-preservation was performed with DMSO (dimethyl-sulfoxide), which serves as an anti-crystallizing agent, and subsequent storage in liquid nitrogen atmosphere at temperatures that should never exceed −140° C. The cryo-preservation medium was composed of 10% DMSO, 10% FBS, and 80% complete R1 medium with the addition of LIF. All the culture handling operations described thus far must be performed under a tissue culture hood (Jupiter, Cell Bio): a constant flow of air in the range of 545-550 m$^3$/h permits operations to be performed in sterile conditions. Sterility is guaranteed by a HEPA filter positioned downstream from the inflow designed to withhold 99.97% of the particles with greater than 0.3 μm diameter.

Engineered Niches

Compared to the experiments conducted by Raimondi et al. (2013 e 2014) featuring single niches spatially distributed differently in hexagonal patterns, the configuration was modified in order to obtain higher niches surface density. Two new sets of niches were produced: the first generation had a continuous matrix of synthetic niches produced by the pairing of single niches that completely covered a 6 mm diameter circular region. This region was enclosed by a PDMS polymer crown that permits the maximization of the area covered by the niches compared to the glass substrate's two-dimensional surface, in this way enabling the coverage of 96% of the total surface (see FIG. 4A). These samples very often present various damages due to the shrinking of the material, which deforms the structure, and to cavitation, which leads to the formation of bubbles and the consequent rupture of the matrix (see FIG. 4B-C). The difficulty in obtaining uniform, defined, and unbroken matrices led to the production of the second generation of set of niches.

After the first generation, in order to reduce the residual stress that determines volumetric reduction during expansion, we decided to reduce the laser-written surface area from 96% to 88% of the surface covered using a new supermatrix configuration made of multiple smaller matrices of 5×5 niches. Maintaining the 2PP setup unaltered, this solution was observed to be sufficient to obtain a practically perfect supermatrix. Furthermore, the second generation permitted a reduction in the time required to obtain the samples: 14 hours against the 17 hours required by the first.

The 2D Controls Structure

The two-dimensional sample is the negative control structure adopted in our experiment, meaning that in this particular condition we expect the cells to completely lose their capacity for self-renewal and generate the expression of the characteristic genes of differentiated phenotype. Glass was selected for the 2D control structure. In order to duplicate the same condition as that of the nichoid sample, also the control structure had a PDMS crown. The crown is obtained by pouring the base and cross-linking solution (10:1) in a metal mold that is inserted in an oven for the baking step conducted at 80° C. for 30-45 minutes as required by the hardness that must be given to the crown. Air-plasma treatment is performed under a tissue culture hood, with an ionizer in order to expose and load the hydroxyl groups (—OH), which in this way are capable of bonding together by ionic bonding with the silicon atom in the glass's siloxane groups.

Sterilization and Seeding

The same sterilization process was used to sterilize the niches and the 2D control structures, and even if it is rather simple, it required the fairly long time of two days to perform. We used a shorter process than the method adopted by Raimondi et al. (2014). The samples were initially positioned in 24-well culture plates with low adhesion in such way that the cells were able to adhere only where either the nichoid or the glass of the 2D control structure was present. The process began with 4 washes in deionized water of 5 minute duration: moistening the wells prior to beginning sterilization operations is recommended because in low adhesion wells the samples exhibit a marked tendency to float. This process continued for 1.5 hours in a 70% ethanol solution with 4 washes of 5 minute duration in D-PBS 1% (Gibco, 14200-067)+Penicillin-Streptomycin (Pen-Strep). At this point, conditioning was performed with a complete R1 medium, and the samples were left under a tissue culture hood overnight with a UV lamp switched on. The day after UV exposure, the samples were ready to be seeded: seeding was performed at 10,000 cell/cm$^2$ density. All operations were performed in sterile conditions.

Characterization of Gene Expression

The samples fixed at the three established measurement time intervals were examined by fluorescence microscopy. The protein associated with the gene was recognized through the primary antibodies that bond directly to the target. Viewing under fluorescence microscopy was enabled by a fluorophore bonded to the secondary antibody that possesses affinity for the primary antibody to which it binds. Stemness and differentiation markers are then used for distinction.

Stemness markers: Oct4 (Octamer-Binding Transcription factor 4), this is the gene that characterizes the state of stemness in the ESc.

Differentiation markers: Smooth Muscle Actinin (α-SMA); NKX2-5, Homeobox-protein NKX2-5; GATA-4; SOX-17; βIII-Tubulin.

Matrix markers: Osteocalcin; Collagen type I.

Microscopic Analysis Technique

The samples were analyzed using various microscope techniques depending on what was to be observed, the degree of detail to be reached, and whether the culture being examined was to be kept alive or not. The types of microscopic analysis adopted were phase contrast microscopy, confocal microscopy, and Scanning Electron Microscope (SEM).

Statistical Analysis

We took 15 measurement photos at 3, 7, and 14 day intervals per marker and per sample (the 2D control structure, the nichoid structure, and the kidney matrix) during the confocal microscopy image acquisition phase. Statistical analyses were performed in a single experiment among the various samples available for a determined marker.

Morphologic Analysis

In addition to fluorescence analysis and the respective quantification, assessments regarding the morphological modifications that cultures undergo during the first two weeks of maintenance in vitro were also conducted. The first type of quantification in this regard is the measurement of the diameters of the colonies present throughout the entire sample for all three types of scaffold.

Results

Morphological Assessment

Time-Course Structural Analysis

The degree to which the adhesion substrate can drastically influence cell behavior and make colonies assume different shapes depending on the surrounding environment is well known. Morphological-structural analysis conducted using phase contrast microscopy and SEM has led to the definition of how the substrates in question—the 2D control structure and the nichoid—contribute in various ways to the structural organization of the cell cultures over time.

The 2D Control Structure

Glass is not the ideal culture substrate for this particular type of cell; small colonies, in fact, clearly visible with phase contrast microscopy at culture day 3, have spherical shapes with clearly defined, scarcely jagged edges indicative of the fact that the few cells that permit adhesion are found at the base of the colony, which however prefers a vertical rather than horizontal development. At around culture day 10, the embryoid bodies (EBs) reach a size characterized by a height that varies from 40 to 60 μm at which vertical development is no longer preferred. Reaching the critical size leads to the loss of roundish configuration and the consequent disaggregation of the EB: the cells therefore begin colonizing the surrounding free substrate and reach confluence in the time of 2-3 days. Direct interaction with the substrate promotes a much more marked and specific degree of differentiation than that of growth in EB configuration. The distribution of cells over the surface during culture demonstrates a type of behavior similar to that of the colonies: initially, these are present in much higher number in the external crown near the PDMS crown. This is largely due to the effect of the crown during seeding: during the filling of the well in which the sample is positioned, in fact, a bubble effect is produced inside the crown that pushes the cells towards the outer part of the culture region where they effectively adhere; for this reason, the central region is scarcely colonized. Distribution throughout the surface remains inhomogeneous until the cellular diffusion derived from the disaggregation of the EB leads to confluence.

Nichoids

The three-dimensional niche environment exerts a different effect on cultures than the 2D control structure. After seeding, the cells precipitate inside the medium until reaching the niche: some cells fall directly into the pores on the top side and adapt to the 3D structure, making use of their podia and protrusions (see FIG. 10), whereas others, where the pores are smaller, stop on the top side without penetrating.

This leads to the creation of two different situations: the cells inside the niche proliferate, perceiving a 3D environment engineered to maintain stemness, whereas the cells outside grow in the form of EB as if a normal 2D substrate were present.

Observing the culture with phase contrast microscopy, these two situations are clearly distinguishable: the colonies inside the niche have characteristic diameters comparable with the size of the niche itself due to the effect of containment that it exerts in five of the six directions of development, whereas the colonies outside the niche, which do not undergo any limiting effect, grow until reaching the critical size. These latter, when observed in time-course, can be seen to move on the top side, varying their conformation and interacting with the other cells that have adhered on the top side. Considering these aspects, we decided to take into consideration during gene expression analysis by confocal microscopy only the niches inside the niches characterized by a limited number of cells and reduced dimensions: only these cells, in fact, perceive the 3D environment and will be capable of maintaining pluripotency.

Two additional types of behavior were observed. The first depended on the fact that the structure exerts a physical limit on five of its six faces and therefore permits the cells to proliferate and migrate from the top side, an event that occurs around culture day 6: from the moment the cells exceed this limit, they behave exactly as described above. The fact is that once the EB has formed, it possesses a certain affinity for the cells in the nichoid and makes a partial contribution to their migration. The second type of behavior regards the EBs themselves: in this case as well, their development comes to a halt once their critical dimension has been reached, at which point they disaggregate. The cells that come from the EB fall back onto the structure and re-populate the niches.

In order to assess the possible re-utilization of the niches just cleaned, it was decided to include them in the fluorescence experiment together with other types of sample. To this purpose, the sample structures were re-sterilized by standard process and then reseeded. The structure did not undergo modification of any kind at all in the second utilization, suggesting that any damage present must be ascribed solely and exclusively to the productive process and not the cell culture.

Colony Diameter Analysis

Because it does not pose any constraint on colony development, the 2D control structure constantly promotes higher average diameters than those of the colonies on the nichoid over time. Furthermore, the two niche configurations seem to affect growth in the same way. One important aspect is the ratio between average colony diameter and characteristic niche dimension. The fact that these two dimensions remain similar provides important indication of the fact that the colonies are effectively inside the niche because they exert, as previously mentioned, a physical containment effect: this is undeniably true for the measurement made at the first time interval. After around 7 days, however, a part of the colonies begins growing beyond the 90 μm containment area, and after 14 days, the formation of EBs has become predominant with the development of colonies above the top side of the niche.

Stemness and Differentiation Marker Assessment

The setting was conducted by culturing mES on 18×18 mm square coverglasses having the same mechanical and surface characteristics as the glass substrate of the 2D control structures and the niches.

The definitive markers used were therefore OCT4, GATA4, NKX2-5, and αSMA. The three differentiation markers all characterize the cardio-myocyte colonies in various ways.

Exp01: First Generation Nichoids

In this first experiment, first generation nichoids were used, in other words, those with surfaces inside the PDMS crown completely written and occupied by the structure. Also niches obtained through trypsinization used in a previous test were tested.

The NKX2-5 cardiac marker was observed to be not expressed in all culture conditions. As regards the other two differentiation markers instead, the expression trend proved to be as expected and already qualitatively assessed on glass in the calibration test. GATA4, in fact, displays the classic up-down-up expression on the 2D control structure, and as already observed, presents high levels at T0, whereas αSMA increases in terms of area as the culture proceeds. Nichoids, instead, demonstrate very different trends for the two markers, but share the characteristic of reducing both. Despite an initial level of GATA4 comparable to that of the control structure, the expression of the gene in successive measurements was completely extinguished in the niche. As regards αSMA instead, the niche was shown to discourage such expression, even if at culture day 14 it was present in minimum degree, but much lower than in the 2D control structure, however. One important aspect is that the differentiation marker results obtained with new and re-utilized nichoids were entirely comparable, and this means that the structure maintains its properties even when it is re-used.

After analyzing differentiation marker trends, the influence of the substrates on cell stemness was studied. The most important result was observed on culture day 7: at both the level of percentage overlap between markers and DAPI and the level of mean intensity, in fact, the niche was observed to promote higher levels of expression of OCT4 than both the other two control structures under study. This confirms that the nichoid's 3D structure is necessary and sufficient (given that no chemical conditioning was provided) to maintain pluripotency. At culture day 14, such effect is no longer due to the phenomenon of the colonies' having exceeded the physical limit that determines the loss of interaction with the controlled 3D environment described above. As regards differentiation markers, new niches and re-utilized niches present entirely comparable results.

In conclusion, the niche was shown to promote pluripotency more than the other two control structures while also inhibiting differentiation. The 2D control structure demonstrated the behaviors expected, promoting the expression of GATA4, and above all, αSMA, which localized on the sides of the colonies in contact with glass, confirming that the stiffness of the substrate is fundamental for its promotion.

Exp02: Nichoid Supermatrix

The same experimental protocol was applied in the second experiment that involved the use of the supermatrix according to the invention (comprising separate matrices of niches). The results confirm those of the previous experiment, with the fundamental advantage of allowing a significant scaling-up of the stem cell culture without the problems caused by rupture due to shrinkage and even a surprising structural stability.

CONCLUSIONS

The impossibility of prior art to keep adult stem cells undifferentiated in prolonged culture places a noteworthy limit on their potential for application in the field of regenerative medicine and tissue engineering. The degree to which substrates with defined three-dimensional structures that mimic the native micro-environment of stem cell niches promote both the maintenance of adult stem cells multipotency in prolonged culture and an isotropic tension state have recently been shown. One of the most relevant results (Example 1) was achieved by seeding MSC on a controlled-geometry niches obtained using the 2PP technique: cell density inside the synthetic niche was shown to be 67% higher than that of the external region, in fact. Furthermore, the cells contained inside it did not express differentiation markers, in this way suggesting that the niche promotes a significant maintenance of stemness.

In another experiment, the effect of the synthetic niches on a more reactive cell population with higher differentiating power than MSC was assessed: murine embryonic stem cells (mESc). In order to assess the effect of synthetic niches on pluripotency and differentiation, two separate substrates were cultured: the niches and a 2D control structure (glass). The cultures were allowed to proceed for 14 days without any chemical conditioning (LIF). The results show that the niche promoted pluripotency maintenance with the expression of OCT4 to a much greater degree than the control structure present while at the same time inhibiting differentiation, characterized by the markers such as GATA4, αSMA, and NKX2-5 that were instead expressed on the glass control. This demonstrates that the synthetic niche is capable of exerting a tension state favorable to maintaining the pluripotency of mESc as well.

Even more significantly, the supermatrix according to the invention maintains the same characteristics of the individual niche, with the fundamental advantage of offering a much larger surface combined with elevated structural stability that increases culture capacity considerably.

The invention claimed is:

1. A supermatrix of synthetic niches comprising at least a first and a second matrix of synthetic niches,
    wherein each matrix comprises n×m synthetic niches,
        wherein n and m, the same or different from each other, independently have a value ≥1, provided that one of m or n is ≥2 and with a maximum value of m and n which allows to maintain a structure of a single synthetic niche intact such that shrinking or contraction of the synthetic niche does not cause a disruption or detachment of a niche matrix, and
    wherein a distance (d) between each synthetic niche matrix and another is greater than zero and
    wherein in each matrix every synthetic niche has one or more walls in common with at least one other synthetic niche of the matrix.

2. The supermatrix of synthetic niches of claim 1, wherein said maximum value for n and m is 100.

3. The supermatrix of synthetic niches of claim 1, wherein m and n have the same value.

4. The supermatrix of synthetic niches of claim 1 wherein the height of the supermatrix of synthetic niches is comprised between about 30 and about 100 μm.

5. The supermatrix of synthetic niches of claim 1, comprising or made of a resin.

6. The supermatrix of synthetic niches of claim 1, wherein the walls of one or more of said synthetic niches are covered with molecules providing a signal inducing maintenance of cell pluripotency and/or with molecules facilitating adhesion of cells to the niche.

7. A multi-well culture plate in which the bottom of said multi-well culture plate is covered by one or more supermatrix of synthetic niches of claim 1.

8. An in vivo implant comprising a supermatrix of synthetic niches of claim 1.

9. The in vivo implant of claim 8, further comprising a cell or a cell population.

10. The in vivo implant of claim 9, wherein the cell or cell population comprises cells derived from or isolated from a patient.

11. The in vivo implant of claim 9, wherein the cell or cell population comprises cultured cells.

12. The supermatrix of synthetic niches of claim 1, wherein the shrinking is caused mechanical stress or deformation.

13. The in vivo implant of claim 9, wherein the cell or cell population comprises a stem cell.

14. The in vivo implant of claim 13, wherein the stem cell is a multipotent or a pluripotent stem cell, or an embryonic stem cell.

15. The supermatrix of synthetic niches of claim 5, wherein the resin comprises a photopolymerizable resin.

16. The supermatrix of synthetic niches of claim 15, wherein the photopolymerizable resin comprises an organic/inorganic hybrid photosensitive material.

17. The supermatrix of synthetic niches of claim 16, wherein the organic/inorganic hybrid photosensitive material comprises an ultra-low shrinkage hybrid photosensitive material.

18. The supermatrix of synthetic niches of claim 15, wherein the photopolymerizable resin comprises methacrylol oxypropyl trimethoxy silane or zirconium propoxide.

19. The supermatrix of synthetic niches of claim 1, wherein the each niche is coated with a hyaluron-based or a gelatin-based hydrogel.

20. The multi-well culture plate of claim 7, wherein the bottom of said multi-well culture plate is coated with perfluoropolyether before covering by one or more supermatrix of synthetic niches of claim 1.

* * * * *